(12) United States Patent
Nellore et al.

(10) Patent No.: US 11,147,801 B2
(45) Date of Patent: *Oct. 19, 2021

(54) METHODS OF USE FOR TRISUBSTITUTED BENZOTRIAZOLE DERIVATIVES AS DIHYDROOROTATE OXYGENASE INHIBITORS

(71) Applicant: Aurigene Discovery Technologies Limited, Bangalore (IN)

(72) Inventors: Kavitha Nellore, Bangalore (IN); Subramanya Hosahalli, Bangalore (IN)

(73) Assignee: Aurigene Discovery Technologies Limited, Karnataka (IN)

(*) Notice: Subject to any disclaimer, the term of this patent is extended or adjusted under 35 U.S.C. 154(b) by 0 days.

This patent is subject to a terminal disclaimer.

(21) Appl. No.: 16/607,609

(22) PCT Filed: Apr. 19, 2018

(86) PCT No.: PCT/IB2018/052710
§ 371 (c)(1),
(2) Date: Oct. 23, 2019

(87) PCT Pub. No.: WO2018/197997
PCT Pub. Date: Nov. 1, 2018

(65) Prior Publication Data
US 2020/0078339 A1 Mar. 12, 2020

Related U.S. Application Data

(63) Continuation of application No. 15/899,707, filed on Feb. 20, 2018, now abandoned, which is a continuation of application No. 15/494,820, filed on Apr. 24, 2017, now Pat. No. 9,937,155.

(51) Int. Cl.
| A61K 31/4192 | (2006.01) |
| A61K 31/454 | (2006.01) |
| A61K 31/496 | (2006.01) |
| A61K 31/5377 | (2006.01) |
| A61P 35/02 | (2006.01) |

(52) U.S. Cl.
CPC ........ *A61K 31/4192* (2013.01); *A61K 31/454* (2013.01); *A61K 31/496* (2013.01); *A61K 31/5377* (2013.01); *A61P 35/02* (2018.01)

(58) Field of Classification Search
CPC ................................................. A61K 31/4192
See application file for complete search history.

(56) References Cited

U.S. PATENT DOCUMENTS

| 6,841,561 | B1 | 1/2005 | Tan et al. |
| 9,630,932 | B2 | 4/2017 | Thunuguntla et al. |
| 9,937,155 | B2 | 4/2018 | Hosahalli |
| 10,080,740 | B2 | 9/2018 | Thunuguntla et al. |
| 2006/0199856 | A1 | 9/2006 | Leban et al. |
| 2008/0287503 | A1 | 11/2008 | Petry et al. |
| 2012/0028959 | A1 | 2/2012 | Thunuguntla et al. |
| 2013/0035329 | A1 | 2/2013 | Saunders et al. |
| 2013/0109643 | A1 | 5/2013 | Riggins et al. |
| 2013/0295198 | A1 | 11/2013 | Claudio et al. |
| 2018/0263970 | A1 | 9/2018 | Sykes et al. |
| 2018/0369206 | A1 | 12/2018 | Nellore et al. |
| 2019/0025313 | A1 | 1/2019 | Si et al. |
| 2019/0105304 | A1 | 4/2019 | Thunuguntla et al. |
| 2021/0088520 | A1 | 3/2021 | Si et al. |
| 2021/0113531 | A1 | 4/2021 | Ulanet et al. |

FOREIGN PATENT DOCUMENTS

| JP | 2004-536122 A | 12/2004 |
| WO | 2006/024034 A1 | 3/2006 |
| WO | 2008/028860 A1 | 3/2008 |
| WO | 2010/081898 A1 | 7/2010 |
| WO | 2010/115736 A2 | 10/2010 |
| WO | 2013/049112 A1 | 4/2013 |
| WO | 2014/128669 A2 | 8/2014 |

(Continued)

OTHER PUBLICATIONS

Akbay et al., D-2-hydroxyglutarate produced by mutant IDH2 causes cardiomyopathy and neurodegeneration in mice. Genes Dev. Mar. 1, 2014;28(5):479-90.
Al-Soud et al., Synthesis and properties of new substituted 1,2,4-triazoles: potential antitumor agents. Bioorg Med Chem. Apr. 17, 2003;11(8):1701-8.
Arnould et al., Checkpoint kinase 1 inhibition sensitises transformed cells to dihydroorotate dehydrogenase inhibition. Oncotarget. Jul. 12, 2017;8(56):95206-95222.
Batt, Inhibitors of dihydroorotate dehydrogenase. Expert Opinion on Therapeutic Patents. 1999;9(1):41-54.

(Continued)

*Primary Examiner* — Karen Cheng
(74) *Attorney, Agent, or Firm* — McCarter & English, LLP; Steven G. Davis; Michael J. DeGrazia

(57) ABSTRACT

The present invention provides methods for treating a cancer in a subject and for inhibiting tumor growth, metastasis or a dihydrorotate oxygenase enzyme activity of a tumor or cancer cell. At least one trisubstituted benzotriazole derivative with the formula (I) is administered to the subject or is contacted with the cancer cell. Compounds of formula (I) have substituents $R_1$, $R_2$ and $R_3$ which have the meanings given in the specification, and pharmaceutically acceptable salts thereof.

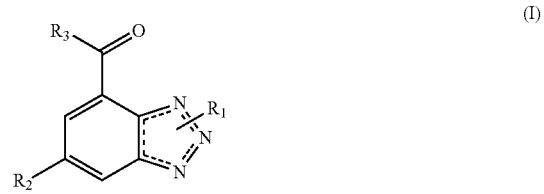

(I)

12 Claims, 11 Drawing Sheets

(56) References Cited

FOREIGN PATENT DOCUMENTS

| WO | 2015/169944 A1 | 11/2015 |
|----|----------------|---------|
| WO | 2017/037022 A1 | 3/2017  |

OTHER PUBLICATIONS

Borodovsky et al., 5-azacytidine reduces methylation, promotes differentiation and induces tumor regression in a patient-derived IDH1 mutant glioma xenograft. Oncotarget. Oct. 2013;4(10):1737-47.

Brown et al., Adaptive Reprogramming of De Novo Pyrimidine Synthesis is a Metabolic Vulnerability in Triple-Negative Breast Cancer. Cancer Discov. Apr. 2017;7(4):391-399.

Cao et al., Targeting of Hematologic Malignancies with PTC299, A Novel Potent Inhibitor of Dihydroorotate Dehydrogenase with Favorable Pharmaceutical Properties. Mol Cancer Ther. Jan. 2019;18(1):3-16.

Castelli et al., New Developments of Differentiation Therapy of Acute Myeloid Leukemia. Current Pharmacogenomics and Personalized Medicine. 2016;14(2):86-105.

Chandrashakara, The treatment strategies of autoimmune disease may need a different approach from conventional protocol: a review. Indian J Pharmacol. Nov.-Dec. 2012;44(6):665-71.

Chaturvedi et al., Mutant IDH1 promotes leukemogenesis in vivo and can be specifically targeted in human AML. Blood. Oct. 17, 2013;122(16):2877-87.

Chemistry Explained, Isomerism. Retrieved online at: http://www.chemistryexplained.com/Hy-Kr/Isomerism.html. 4 pages, (2016).

Christian et al., The novel dihydroorotate dehydrogenase (DHODH) inhibitor BAY 2402234 triggers differentiation and is effective in the treatment of myeloid malignancies. Leukemia. Oct. 2019;33(10):2403-2415.

Dang et al., Cancer-associated IDH1 mutations produce 2-hydroxyglutarate. Nature. Dec. 10, 2009;462(7274):739-44.

Dexter et al., Activity of a novel 4-quinolinecarboxylic acid, NSC 368390 [6-fluoro-2-(2'-fluoro-1,1'-biphenyl-4-yl)-3-methyl-4-quinolinecarb oxylic acid sodium salt], against experimental tumors. Cancer Res. Nov. 1985;45(11 Pt 1):5563-8.

Elsayed et al., Prognostic value of IDH1 mutations identified with PCR-RFLP assay in acute myeloid leukemia patients. J Egypt Natl Canc Inst. Mar. 2014;26(1):43-9.

Emadi et al., Presence of isocitrate dehydrogenase mutations may predict clinical response to hypomethylating agents in patients with acute myeloid leukemia. Am J Hematol. May 2015;90(5):E77-9.

Golub et al., Molecular classification of cancer: class discovery and class prediction by gene expression monitoring. Science. Oct. 15, 1999;286(5439):531-7.

Jin et al., Cancer-associated IDH1 and IDH2 mutations: therapeutic opportunities. EJC Supplement. Nov. 17, 2010;8(7):56. Poster 160.

Kinnaird et al., Metabolic modulation of cancer: a new frontier with great translational potential. J Mol Med (Berl). Feb. 2015;93(2):127-42.

Koundinya et al., Dependence on the Pyrimidine Biosynthetic Enzyme DHODH is a Synthetic Lethal Vulnerability in Mutant KRAS-Driven Cancers. Cell Chem Biol. Jun. 21, 2018;25(6):705-717.

Ladds et al., A DHODH inhibitor increases p53 synthesis and enhances tumor cell killing by p53 degradation blockage. Nat Commun. Mar. 16, 2018;9(1):1107.

Li et al., The effects of teriflunomide on lymphocyte subpopulations in human peripheral blood mononuclear cells in vitro. J Neuroimmunol. Dec. 15, 2013;265(1-2):82-90.

Liu et al., Structures of human dihydroorotate dehydrogenase in complex with antiproliferative agents. Structure. Jan. 15, 2000;8(1):25-33.

Luengo et al., Targeting Metabolism for Cancer Therapy. Cell Chem Biol. Sep. 21, 2017;24(9):1161-1180.

Madak et al., Revisiting the role of dihydroorotate dehydrogenase as a therapeutic target for cancer. Pharmacol Ther. Mar. 2019;195:111-131. Pre-publication edition.

Mathur et al., PTEN Regulates Glutamine Flux to Pyrimidine Synthesis and Sensitivity to Dihydroorotate Dehydrogenase Inhibition. Cancer Discov. Apr. 2017;7(4):380-390.

McClean et al., Multiple inhibitor analysis of the brequinar and leflunomide binding sites on human dihydroorotate dehydrogenase. Biochemistry. Feb. 20, 2001;40(7):2194-200.

Munier-Lehmann et al., On dihydroorotate dehydrogenases and their inhibitors and uses. J Med Chem. Apr. 25, 2013;56(8):3148-67.

NIH—National Cancer Institute, Targeted Cancer Therapies. Retrieved online at: http://www.cancer.gov/aboutcancer/treatment/types/targetedtherapies/targetedtherapiesfactsheet. 6 pages, Apr. 25, 2014.

Ravandi et al., Prognostic significance of alterations in IDH enzyme isoforms in patients with AML treated with high-dose cytarabine and idarubicin. Cancer. May 15, 2012;118(10):2665-73.

Ringshausen et al., The immunomodulatory drug Leflunomide inhibits cell cycle progression of B-CLL cells. Leukemia. Mar. 2008;22(3):635-8.

Rohle et al., An inhibitor of mutant IDH1 delays growth and promotes differentiation of glioma cells. Science. May 3, 2013;340(6132):626-30.

Ruckemann et al., Leflunomide inhibits pyrimidine de novo synthesis in mitogen-stimulated T-lymphocytes from healthy humans. J Biol Chem. Aug. 21, 1998;273(34):21682-91.

Sykes et al., Inhibition of Dihydroorotate Dehydrogenase Overcomes Differentiation Blockade in Acute Myeloid Leukemia. Cell. Sep. 22, 2016;167(1):171-186.e1-e8.

Turcan et al., Efficient induction of differentiation and growth inhibition in IDH1 mutant glioma cells by the DNMT Inhibitor Decitabine. Oncotarget. Oct. 2013;4(10):1729-36.

Ullrich et al., Recombinant expression of N-terminal truncated mutants of the membrane bound mouse, rat and human flavoenzyme dihydroorotate dehydrogenase. A versatile tool to rate inhibitor effects? Eur J Biochem. Mar. 2001;268(6):1861-8.

Vyas et al., Recent developments in the medicinal chemistry and therapeutic potential of dihydroorotate dehydrogenase (DHODH) inhibitors. Mini Rev Med Chem. Oct. 2011;11(12):1039-55.

Walse et al., The structures of human dihydroorotate dehydrogenase with and without inhibitor reveal conformational flexibility in the inhibitor and substrate binding sites. Biochemistry. Aug. 26, 2008;47(34):8929-36.

Wang et al., Targeted inhibition of mutant IDH2 in leukemia cells induces cellular differentiation. Science. May 3, 2013;340(6132):622-6.

Woo et al., The antilymphocytic activity of brequinar sodium and its potentiation by cytidine. Effects on lymphocyte proliferation and cytokine production. Transplantation. Aug. 1993;56(2):374-81.

Yamaguchi et al., IDH1 and IDH2 mutations confer an adverse effect in patients with acute myeloid leukemia lacking the NPM1 mutation. Blood. 2013;122(21):4977.

Zeng et al., Targeting dihydroorotate dehydrogenase in acute myeloid leukemia. Haematologica. Sep. 2018;103(9):1415-1417.

International Search Report and Written Opinion for Application No. PCT/IB2018/052710, dated Jul. 16, 2018, 8 pages.

Matsuda et al., Distinct global DNA methylation status in B-cell lymphomas: immunohistochemical study of 5-methylcytosine and 5-hydroxymethylcytosine. J Clin Exp Hematop. 2014;54(1):67-73.

McDonald et al., Selective Vulnerability to Pyrimidine Starvation in Hematologic Malignancies Revealed by AG-636, a Novel Clinical-Stage Inhibitor of Dihydroorotate Dehydrogenase. Mol Cancer Ther. 2020;19:2502-15.

Baumann et al., Dihydroorotate dehydrogenase inhibitor A771726 (leflunomide) induces apoptosis and diminishes proliferation of multiple myeloma cells. Mol Cancer Ther. Feb. 2009;8(2):366-75.

METHODS OF USE FOR TRISUBSTITUTED BENZOTRIAZOLE DERIVATIVES AS DIHYDROOROTATE OXYGENASE INHIBITORS

CROSS-REFERENCE TO RELATED APPLICATIONS

This application is a 35 U.S.C. § 371 national stage filing of International Application No. PCT/IB2018/052710, filed on Apr. 19, 2018 which in turn claims priority to U.S. patent application Ser. No. 15/899,707, filed Feb. 20, 2018, and U.S. patent application Ser. No. 15/494,820, filed Apr. 24, 2017 and now U.S. Pat. No. 9,937,155. The entire contents of each of the foregoing applications are hereby incorporated by reference.

BACKGROUND OF THE INVENTION

Field of the Invention

The present invention relates to novel trisubstituted benzotriazole derivatives of formula (I) which are inhibitors of dihydroorotate dehydrogenase. In particular, the invention refers to novel compounds, which inhibit DHODH enzyme activity, to a process for their manufacture and pharmaceutical compositions containing them, and to their use for the treatment and prevention in diseases or disorder, in particular their use in diseases or disorder where there is an advantage in inhibiting DHODH.

Description of the Related Art

DHODH is a protein that catalyzes one of the steps in the denovo pyrimidine nucleotide biosynthetic pathway. (Greene et al. Biochem Pharmacol 1995, 50:861-7; Davis J. P et al. FASEB J 1996, 10(6): Abst C23). It catalyzes the only oxidation/reduction reaction in that pathway, which is the step of converting DHO (dihydroorotate) to orotate with the aid of flavin cofactor and an electron acceptor. Inhibitors of dihydroorotate dehydrogenase have been found to possess wider applications as chemotherapeutic agents. (Kensler et al. 1989 in: Design of Enzyme Inhibitors as Drugs; Sandler, M., and Smith, H. J. Eds., pp 379-401 Oxford Univ Press, Oxford England; Cody et al. Am. J. Clin. Oncol. 16, 526-528 (1993)).

As an example for DHODH inhibitors, the quinoline derivative Brequinar (6-Fluoro-2-(2'-fluoro[1,1'-biphenyl]-4-yl)-3-methyl-4-quinolinecarboxylic acid) exhibits an anticancer activity towards L1210 murine leukemia (Andreson L W. Et al. Cancer Commun. 1989; 1(6), 381-7; Chen S F. et al. Cancer Res. 1986 October; 46(10): 5014-9). It has also been shown that Brequinar potentiates 5-fluorouracil antitumor activity in a murine model colon 38 tumor by tissue-specific modulation of uridine nucleotide pools. (G Pizzorno et al. Cancer Res. 1992 Apr 1; 52:1660-5).

DHODH inhibitors may also be useful in the treatment of viral mediated diseases (see U.S. Pat. No. 6,841,561). Furthermore, inhibition of DHODH is known to be a promising target for treating transplant rejection, rheumatoid arthritis, psoriasis as well as autoimmune diseases (Kovarik, J. M. et al. Expert Opin. Emerg. Drugs 2003, 8, 47; Allison, A. C. Transplantation Proc. (1993) 25(3) Suppl. 2, 8-18); Makowka, L., Immunolog Rev. (1993) 136, 51-70; Davis J. P et al. Biochemistry 1996, 35: 1270-3).

Leflunomide, a well known DHODH inhibitor is a synthetic drug currently marketed, a low-molecular weight drug of the isoxazole class (see EP0527736, JP1993506425, JP1999322700, JP1999343285, U.S. Pat. Nos. 5,494,911, 5,532,259, WO19991017748) and used in the treatment of Rheumatoid arthritis and is also under evaluation for use in the treatment of inflammatory bowel disease and chronic allograft rejection.

In vivo, Leflunomide is quickly transformed into its active metabolite Teriflunomide that exerts its anti-inflammatory, antiproliferative and immunosuppressive effects via mechanisms that are not completely understood. Teriflunomide is not only a potential inhibitor of protein tyrosine kinase in vivo but a 100-1,000-fold greater inhibitor of DHODH (Davis J. P et al. FASEB J 1996, 10(6): Abst C23; Davis J. P et al. Biochemistry 1996, 35:1270-3).

With the rise in number of patients affected by autoimmune and related diseases, there is unmet need for new drugs that can treat such diseases more effectively. There is still a crucial need for immunosuppressive agents, that are further useful in a wide variety of autoimmune and chronic inflammatory diseases, including systemic lupus erythematosus, chronic rheumatoid arthritis, multiple sclerosis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. They may also be useful as part of chemotherapeutic regimens for the treatment of cancers, lymphomas and leukemias, alone or in combination with antitumoral compounds well known by the one skilled in the art.

SUMMARY OF THE INVENTION

The present invention is directed to a method for treating a cancer in a subject in need of such treatment. In one embodiment, the cancer is selected from acute myeloid leukemia, multiple myeloma, B-prolymphocytic leukemia, acute lymphoblastic leukemia, chronic lymphocytic leukemia, Hodgkin's disease, non-Hodgkin's lymphoma, follicular lymphoma, diffuse large B cell lymphoma, anaplastic large cell lymphoma, mantle cell lymphoma, lung cancer, breast cancer, triple negative breast cancer, melanoma, glioblastoma, prostate cancer, colon cancer, pancreatic cancer, bone cancer, cancer of the head or neck, skin cancer, cutaneous or intraocular malignant endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancer, and a PTEN mutant cancer. In another embodiment, the cancer is selected from acute myeloid leukemia, multiple myeloma, B-prolymphocytic leukemia, non-Hodgkin's lymphoma, diffuse large B cell lymphoma, anaplastic large cell lymphoma, mantle cell lymphoma, triple negative breast cancer, melanoma, prostate cancer, and cancer of the esophagus. The method comprises the step of administering to the subject one or more times a therapeutically effective amount of at least one compound according to formula (I):

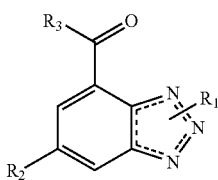

(I)

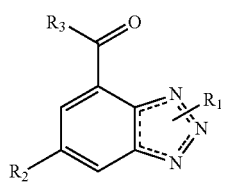

(I)

or a pharmaceutically acceptable salt thereof. In the structure the dotted lines [....] in the ring may represent an optional bond which may be present in any stable combination. $R_1$ may be hydrogen and alkyl. $R_2$ may be -A-$R_4$. A may be arylene or tetrasubstituted arylene where the substituent is halogen. $R_3$ may be hydroxy and amino. $R_4$ may be an optionally substituted aryl and an optionally substituted heteroaryl. The optional substituents may be one or more $R_5$. $R_5$ may be alkyl and —$(CH_2)_nN(R_a)R_b$. $R_a$ and $R_b$ may be independently hydrogen, alkyl and —C(O)alkyl or, alternatively, $R_a$ and $R_b$ can be taken together with the nitrogen atom to which they are attached to form an optionally substituted 4-6 membered heterocyclyl containing 0-2 additional heteroatoms independently selected from O and N where the optional substituent is alkyl and 'n' may be an integer 0 and 1.

The present invention also is directed to a method for inhibiting growth and/or metastasis of tumor cells in a subject. The method comprises the step of administering to the subject one or more times a therapeutically effective amount of at least one compound according to formula (I):

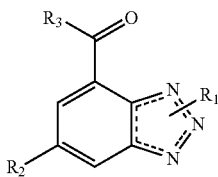

(I)

or a pharmaceutically acceptable salt thereof. In the structure the dotted lines [....] in the ring may represent an optional bond which may be present in any stable combination. $R_1$ may be hydrogen and alkyl. $R_2$ may be -A-$R_4$. A may be arylene or tetrasubstituted arylene where the substituent is halogen. $R_3$ may be hydroxy and amino. $R_4$ may be an optionally substituted aryl and an optionally substituted heteroaryl. The optional substituents may be one or more $R_5$. $R_5$ may be alkyl and —$(CH_2)_nN(R_a)R_b$. $R_a$ and $R_b$ may be independently hydrogen, alkyl and —C(O)alkyl or, alternatively, $R_a$ and $R_b$ can be taken together with the nitrogen atom to which they are attached to form an optionally substituted 4-6 membered heterocyclyl containing 0-2 additional heteroatoms independently selected from O and N where the optional substituent is alkyl and 'n' may be an integer 0 and 1.

The present invention is directed further to a method for inhibiting a dihydrorotate oxygenase enzyme activity in a tumor cell. The method comprises the step of contacting the tumor cell one or more times with a therapeutically effective amount of at least one compound according to formula (I):

or a pharmaceutically acceptable salt thereof. In the structure the dotted lines [....] in the ring may represent an optional bond which may be present in any stable combination. $R_1$ may be hydrogen and alkyl. $R_2$ may be -A-$R_4$. A may be arylene or tetrasubstituted arylene where the substituent is halogen. $R_3$ may be hydroxy and amino. $R_4$ may be an optionally substituted aryl and an optionally substituted heteroaryl. The optional substituents may be one or more $R_5$. $R_5$ may be alkyl and —$(CH_2)_nN(R_a)R_b$. $R_a$ and $R_b$ may be independently hydrogen, alkyl and —C(O)alkyl or, alternatively, $R_a$ and $R_b$ can be taken together with the nitrogen atom to which they are attached to form an optionally substituted 4-6 membered heterocyclyl containing 0-2 additional heteroatoms independently selected from O and N where the optional substituent is alkyl and 'n' may be an integer 0 and 1.

DETAILED DESCRIPTION OF THE INVENTION

Figure 1:
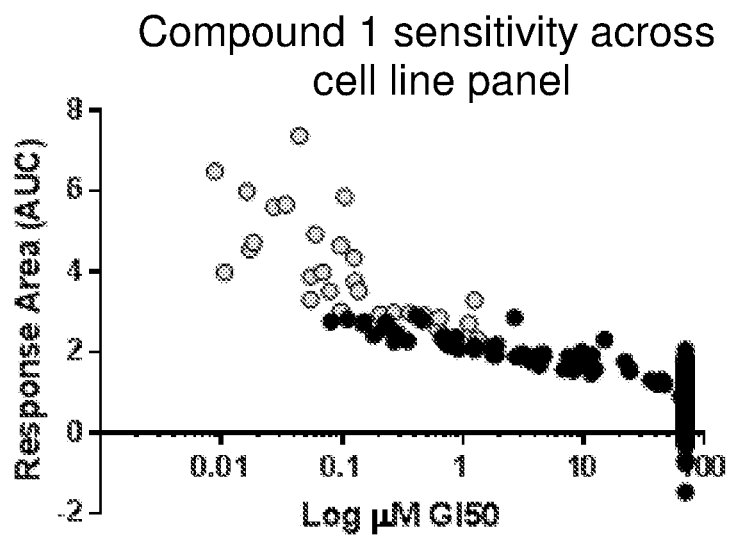
FIG. 1 shows the sensitivity of a panel of ~400 human cancer lines of hemapoietic and non-hemapoietic origin towards growth inhibition by Compound 1 of the invention. Grey circles represent cell lines scored as sensitive (exhibiting ≥75% maximal growth inhibition and a GI50 value<1.5 μM.

In an embodiment, the present invention provides trisubstituted benzotriazole derivatives as dihydroorotate oxygenase inhibitors.

These derivatives are useful as medicament in treatment of autoimmune and inflammatory disorders such as multiple sclerosis, rheumatoid arthritis and diseases like cancer.

In a particular embodiment, the present invention provides compounds of formula (I),

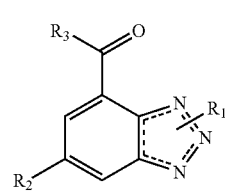

(I)

or a pharmaceutically acceptable salt or a pharmaceutically acceptable regioisomer thereof, wherein;

the dotted lines [....] in the ring represent an optional bond which may be present in any stable combination;

$R_1$ is selected from hydrogen and alkyl;

$R_2$ is $-A-R_4$;

A is arylene or tetrasubstituted arylene; wherein the substituent is halogen;

$R_3$ is selected from hydroxy and amino;

$R_4$ is selected from optionally substituted aryl and optionally substituted heteroaryl; wherein the optional substituents are selected from one or more $R_5$;

$R_5$ is selected from alkyl and $-(CH_2)_nN(R_a)R_b$;

$R_a$ and $R_b$ are independently selected from hydrogen, alkyl and $-C(O)$alkyl;

alternatively $R_a$ and $R_b$ can be taken together with the nitrogen atom to which they are attached to form an optionally substituted 4-6 membered heterocyclyl containing 0-2 additional heteroatoms independently selected from O and N; wherein the optional substituent is alkyl; and 'n' is an integer selected from 0 and 1.

The embodiments below are illustrative of the present invention and are not intended to limit the claims to the specific embodiments exemplified.

According to one embodiment, specifically provided are compounds of formula (I), in which $R_1$ is alkyl; in particular alkyl is methyl.

According to another embodiment, specifically provided are compounds of formula (I), in which $R_2$ is $-A-R_4$, in which -A- is selected from arylene and tetrasubstituted arylene.

According to preceding embodiment, specifically provided are compounds of formula (I), in which $R_2$ is selected from

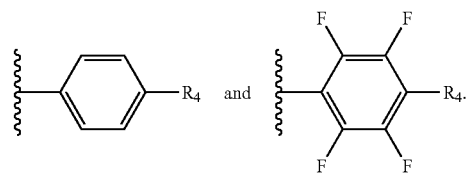

According to one of the preceding embodiment, specifically provided are compounds of formula (I), in which $R_4$ is selected from optionally substituted phenyl; in which optional substituents are selected from methyl, acetylamino, isopropylaminomethyl, methylaminomethyl, dimethylaminomethyl,

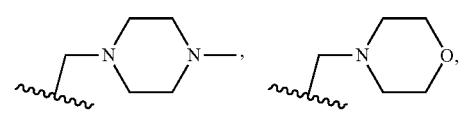

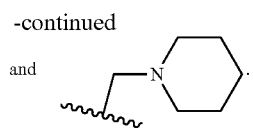 and

According to one of the preceding embodiment, specifically provided are compounds of formula (I), in which $R_4$ is selected from 2,5-dimethyl-1H-pyrrole; According to yet another embodiment, specifically provided are compounds of formula (I), in which $R_3$ is —OH and —NH$_2$.

According to yet another particular embodiment, the compound of formula (I) is a compound of formula (Ia)

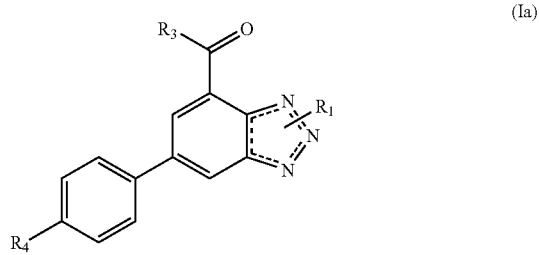

(Ia)

wherein, the dotted line [---], $R_1$, $R_3$ and $R_4$ are same as described in formula (I).

According to yet another particular embodiment, the compound of formula (I) is a compound of formula (Ib)

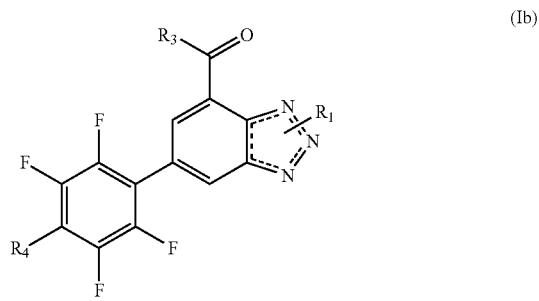

(Ib)

wherein, the dotted line [---], $R_1$, $R_3$ and $R_4$ are same as described in formula (I).

In another embodiment of the present invention, it provides the process for preparation of trisubstituted benzotriazole derivatives of formula (I).

The procedure for the compounds of formula (I) is detailed herein below in the specification stepwise including the general synthesis of various intermediates involved in the process of manufacture of the compounds according to the present invention.

More particularly, the invention provides use of compounds of formula (I) or a pharmaceutically acceptable salt or a regioisomer thereof, including mixtures thereof in all ratios as a medicament, by inhibiting dihydroorotate oxygenase enzyme activity in treating disorder like multiple sclerosis and other diseases such as inflammatory disorders, rheumatoid arthritis and cancer.

Trisubstituted benzotriazole derivatives of formula (I) of the present invention possess therapeutic role of inhibiting the dihydroorotate dehydrogenase (DHODH or DHOD) enzyme. The compounds of formula (I) may be useful for treating and/or preventing, but not restricted to, autoimmune and chronic inflammatory diseases, including systemic lupus erythematosus, chronic rheumatoid arthritis, multiple sclerosis, type I diabetes mellitus, inflammatory bowel diseases, biliary cirrhosis, uveitis and other disorders such as Crohn's diseases, ulcerative colitis, bullous pemphigoid, sarcoidosis, psoriasis, autoimmune myositis, Wegener's granulomatosis, ichthyosis, Graves ophthalmopathy, atopic dermatitis and asthma. The compounds of formula (I) and related formulae can be also useful as part of chemotherapeutic regimens for the treatment of cancers, lymphomas and leukemias alone or in combination with classic antitumoral compounds well known by the one skilled in the art.

Without limiting the scope of present invention, the following definitions are provided in order to aid those skilled in the art in understanding the detailed description of the present invention.

"Alkyl" refers to a hydrocarbon chain that may be a linear or branched chain, containing the indicated number of carbon atoms, for example, a $C_1$-$C_6$ alkyl group may have from 1 to 6 (inclusive) carbon atoms in it. Examples of $C_1$-$C_4$ and $C_1$-$C_6$ alkyl groups include, but are not limited to, methyl, ethyl, propyl, butyl, pentyl, hexyl, isopropyl, isobutyl, sec-butyl, tert-butyl, isopentyl, neopentyl, and isohexyl. An alkyl group can be unsubstituted or substituted with one or more suitable groups.

"Amino" refers to an —N— group, the nitrogen atom of said group being attached to a hydrogen, alkyl, cycloalkyl, aryl, heterocyclyl or any suitable groups. Representative examples of an amino group include, but are not limited to —NH$_2$, —NHCH$_3$ and —NH— cyclopropyl. An amino group can be unsubstituted or substituted with one or more of the suitable groups.

"Aryl" refers to an optionally substituted monocylic, bicyclic or polycyclic aromatic carbocyclic ring system of about 6 to 14 carbon atoms. Examples of a $C_6$-$C_{14}$ aryl group include, but are not limited to phenyl, naphthyl, biphenyl, anthryl, tetrahydronaphthyl, fluorenyl, indanyl, biphenylenyl, and acenaphthyl. Aryl group which can be unsubstituted or substituted with one or more suitable groups.

"Arylene" denotes a divalent monocyclic or bicyclic, saturated, unsaturated or aromatic carbocyclic ring having 6 to 14 carbon atoms which may be unsubstituted or substituted with one or more suitable groups.

"Halogen" or "halo" includes fluorine, chlorine, bromine or iodine.

"Hydroxy" refers to —OH group.

The term "Heterocyclyl" includes the definitions of "heterocycloalkyl" and "heteroaryl". The term "Heterocycloalkyl" refers to a non-aromatic, saturated or partially saturated, monocyclic or polycyclic ring system of 3 to 10 member having at least one heteroatom or heterogroup selected from O, N, S, S(O), S(O)$_2$, NH and C(O). Exemplary heterocycloalkyl groups include piperdinyl, piperazinyl, morpholinyl, thiomorpholinyl, 1,3-dioxolanyl, 1,4-dioxanyl and the like. A heterocycloalkyl group can be unsubstituted or substituted with one or more suitable groups.

"Heteroaryl" refers to an unsaturated, monocyclic, bicyclic, or polycyclic aromatic ring system containing at least one heteroatom selected from oxygen, sulphur and nitrogen. Examples of $C_5$-$C_{10}$ heteroaryl groups include furan, thiophene, indole, azaindole, oxazole, thiazole, thiadiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic heteroaryl groups include those where a phenyl, pyridine, pyrimidine or pyridazine ring is fused to a 5 or 6-membered monocyclic heterocyclyl ring having one or two nitrogen atoms in the ring, one nitrogen atom together with either one oxygen or one sulfur atom in the ring, or one O or S ring atom. A heteroaryl group can be unsubstituted or substituted with one or more suitable groups.

"Hetero atom" refers to a sulfur, nitrogen or oxygen atom.

"Optionally substituted or substituted" as used herein means that at least one hydrogen atom of the optionally substituted group has been substituted with suitable substitutions as exemplified but not limited to halogen, nitro, cyano, hydroxy, oxo (=O), thio (=S), —N($C_1$-$C_3$alkyl)C(O)($C_1$-$C_6$alkyl), —NHC(O)($C_1$-$C_6$alkyl), —NHC(O)(cycloalkyl), —NHC(O)(aryl), —NHC(O)(heterocyclyl), —NHC(O)(heteroaryl), —NHC(O)H, —C(O)$NH_2$, —C(O)NH($C_1$-$C_6$alkyl), —C(O)NH(cycloalkyl), —C(O)NH(heterocyclyl), —C(O)NH(heteroaryl), —C(O)N($C_1$-$C_6$alkyl)($C_1$-$C_6$alkyl), —S(O)NH($C_1$-$C_6$alkyl), —S(O)$_2$NH($C_1$-$C_6$alkyl), —S(O)NH(cycloalkyl), —S(O)$_2$NH(cycloalkyl), carboxy, —C(O)O($C_1$-$C_6$alkyl), —C(O)($C_1$-$C_6$alkyl), =N—OH, substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted heteroaryl, substituted or unsubstituted heterocyclyl, substituted or unsubstituted heteroarylalkyl, substituted or unsubstituted heterocyclic ring.

The particular compounds of the present invention without departing from the scope of the definitions given under compounds of formula (I) and particular compounds emanated from formula (I) are summarized herein below table encompassing the entirety of the scope of compounds within compound of formula (I).

| Compd No. | IUPAC Name |
|---|---|
| 1. | 1-methyl-5-(2'-methyl-[1,1'-biphenyl]-4-yl)-1H-benzo[d][1,2,3]triazole-7-carboxylic acid; |
| 2. | 1-methyl-5-(2'-methyl-[1,1'-biphenyl]-4-yl)-1H-benzo[d][1,2,3]triazole-7-carboxamide; |
| 3. | 5-([1,1'-biphenyl]-4-yl)-1-methyl-1H-benzo[d][1,2,3]triazole-7-carboxylic acid; |
| 4. | 6-([1,1'-biphenyl]-4-yl)-2-methyl-2H-benzo[d][1,2,3]triazole-4-carboxylic acid; |
| 5. | 6-([1,1'-biphenyl]-4-yl)-1H-benzo[d][1,2,3]triazole-4-carboxylic acid; |
| 6. | 6-([1,1'-biphenyl]-4-yl)-1H-benzo[d][1,2,3]triazole-4-carboxamide; |
| 7. | 6-([1,1'-biphenyl]-4-yl)-1-methyl-1H-benzo[d][1,2,3]triazole-4-carboxylic acid; |
| 8. | 2-methyl-6-(2'-methyl-[1,1'-biphenyl]-4-yl)-2H-benzo[d][1,2,3]triazole-4-carboxylic acid; |
| 9. | 1-methyl-6-(2'-methyl-[1,1'-biphenyl]-4-yl)-1H-benzo[d][1,2,3]triazole-4-carboxylic acid; |
| 10. | 1-methyl-6-(2'-methyl-[1,1'-biphenyl]-4-yl)-1H-benzo[d][1,2,3]triazole-4-carboxamide; |
| 11. | 2-methyl-6-(2'-methyl-[1,1'-biphenyl]-4-yl)-2H-benzo[d][1,2,3]triazole-4-carboxamide; |
| 12. | 5-(4-(2,5-dimethyl-1H-pyrrol-1-yl)phenyl)-1-methyl-1H-benzo[d][1,2,3]triazole-7-carboxylic acid; |
| 13. | 6-(4-(2,5-dimethyl-1H-pyrrol-1-yl)phenyl)-2-methyl-2H-benzo[d][1,2,3]triazole-4-carboxylic acid; |
| 14. | 6-(4-(2,5-dimethyl-1H-pyrrol-1-yl)phenyl)-1-methyl-1H-benzo[d][1,2,3]triazole-4-carboxylic acid; |
| 15. | 1-methyl-5-(3'-(morpholinomethyl)-[1,1'-biphenyl]-4-yl)-1H-benzo[d][1,2,3]triazole-7-carboxylic acid; |
| 16. | 2-methyl-6-(3'-(morpholinomethyl)-[1,1'-biphenyl]-4-yl)-2H-benzo[d][1,2,3]triazole-4-carboxylic acid; |
| 17. | 1-methyl-5-(3'-(pyrrolidin-1-ylmethyl)-[1,1'-biphenyl]-4-yl)-1H-benzo[d][1,2,3]triazole-7-carboxylic acid; |
| 18. | 1-methyl-6-(3'-(morpholinomethyl)-[1,1'-biphenyl]-4-yl)-1H-benzo[d][1,2,3]triazole-4-carboxylic acid; |
| 19. | 1-methyl-5-(2,3,5,6-tetrafluoro-[1,1'-biphenyl]-4-yl)-1H-benzo[d][1,2,3]triazole-7-carboxylic acid; |
| 20. | 1-methyl-6-(3'-(piperidin-1-ylmethyl)-[1,1'-biphenyl]-4-yl)-1H-benzo[d][1,2,3]triazole-4-carboxylic acid; |
| 21. | 1-methyl-6-(3'-(pyrrolidin-1-ylmethyl)-[1,1'-biphenyl]-4-yl)-1H-benzo[d][1,2,3]triazole-4-carboxylic acid; |
| 22. | 1-methyl-5-(3'-((4-methylpiperazin-1-yl)methyl)-[1,1'-biphenyl]-4-yl)-1H-benzo[d][1,2,3]triazole-7-carboxylic acid; |
| 23. | 2-methyl-6-(3'-(piperidin-1-ylmethyl)-[1,1'-biphenyl]-4-yl)-2H-benzo[d][1,2,3]triazole-4-carboxylic acid; |
| 24. | 2-methyl-6-(2,3,5,6-tetrafluoro-[1,1'-biphenyl]-4-yl)-2H-benzo[d][1,2,3]triazole-4-carboxylic acid; |
| 25. | 1-methyl-5-(2'-(morpholinomethyl)-[1,1'-biphenyl]-4-yl)-1H-benzo[d][1,2,3]triazole-7-carboxylic acid; |
| 26. | 2-methyl-6-(2'-(morpholinomethyl)-[1,1'-biphenyl]-4-yl)-2H-benzo[d][1,2,3]triazole-4-carboxylic acid; |
| 27. | 1-methyl-5-(2'-(pyrrolidin-1-ylmethyl)-[1,1'-biphenyl]-4-yl)-1H-benzo[d][1,2,3]triazole-7-carboxylic acid; |
| 28. | 2-methyl-6-(2'-(pyrrolidin-1-ylmethyl)-[1,1'-biphenyl]-4-yl)-2H-benzo[d][1,2,3]triazole-4-carboxylic acid; |

| Compd No. | IUPAC Name |
| --- | --- |
| 29. | 1-methyl-5-(2'-((4-methylpiperazin-1-yl)methyl)-[1,1'-biphenyl]-4-yl)-3a,7a-dihydro-1H-benzo[d][1,2,3]triazole-7-carboxylic acid; |
| 30. | 2-methyl-6-(2'-((4-methylpiperazin-1-yl)methyl)-[1,1'-biphenyl]-4-yl)-2H-benzo[d][1,2,3]triazole-4-carboxylic acid; |
| 31. | 1-methyl-5-(4'-(morpholinomethyl)-[1,1'-biphenyl]-4-yl)-1H-benzo[d][1,2,3]triazole-7-carboxylic acid; |
| 32. | 5-(3'-acetamido-[1,1'-biphenyl]-4-yl)-1-methyl-1H-benzo[d][1,2,3]triazole-7-carboxylic acid; |
| 33. | 1-methyl-5-(2,3,5,6-tetrafluoro-3'-(morpholinomethyl)-[1,1'-biphenyl]-4-yl)-1H-benzo[d][1,2,3]triazole-7-carboxylic acid; |
| 34. | 1-methyl-5-(2,3,5,6-tetrafluoro-3'-(piperidin-1-ylmethyl)-[1,1'-biphenyl]-4-yl)-1H-benzo[d][1,2,3]triazole-7-carboxylic acid.2,2,2-trifluoroacetic acid; |
| 35. | 1-methyl-5-(2,3,5,6-tetrafluoro-3'-((4-methylpiperazin-1-yl)methyl)-[1,1'-biphenyl]-4-yl)-1H-benzo[d][1,2,3]triazole-7-carboxylic acid; |
| 36. | 1-methyl-5-(2,3,5,6-tetrafluoro-3'-((isopropylamino)methyl)-[1,1'-biphenyl]-4-yl)-1H-benzo[d][1,2,3]triazole-7-carboxylic acid; |
| 37. | 1-methyl-5-(2,3,5,6-tetrafluoro-3'-((methylamino)methyl)-[1,1'-biphenyl]-4-yl)-1H-benzo[d][1,2,3]triazole-7-carboxylic acid; |
| 38. | 2-methyl-6-(2,3,5,6-tetrafluoro-3'-(piperidin-1-ylmethyl)-[1,1'-biphenyl]-4-yl)-2H-benzo[d][1,2,3]triazole-4-carboxylic acid; |
| 39. | 2-methyl-6-(2,3,5,6-tetrafluoro-3'-(morpholinomethyl)-[1,1'-biphenyl]-4-yl)-2H-benzo[d][1,2,3]triazole-4-carboxylic acid; and |
| 40. | 5-(3'-((dimethylamino)methyl)-2,3,5,6-tetrafluoro-[1,1'-biphenyl]-4-yl)-1-methyl-1H-benzo[d][1,2,3]triazole-7-carboxylic acid, | or a pharmaceutically acceptable salt thereof or a pharmaceutically acceptable regioisomer thereof.

In yet another embodiment, the present invention relates to compounds of formula (I) for use in the treatment of inflammatory disorders and autoimmune diseases or overactive immune response. More preferably, the present invention relates to the use of compounds of formula (I) for the treatment of multiple sclerosis, rheumatoid arthritis and transplant rejection.

Further embodiments of the invention includes use of compounds of formula (I) or pharmaceutically acceptable derivatives, salts and regioisomers thereof, including mixtures thereof in all ratios as a medicament.

Use of compounds as above and pharmaceutically usable derivatives, salts and regioisomers thereof, including mixtures thereof in all ratios, for the preparation of a medicament for the treatment and/or prophylaxis of a dihydroorotate dehydrogenase associated disorder.

Use of compounds as above wherein the dihydroorotate dehydrogenase associated disorder is an autoimmune disorder or condition associated with an overactive immune response.

Use of compounds as above and pharmaceutically usable derivatives, salts and regioisomers thereof, including mixtures thereof in all ratios, for the preparation of a medicament for the treatment and/or prophylaxis of an immunoregulatory abnormality.

Use of compounds as above wherein the immunoregulatory abnormality is multiple sclerosis or rheumatoid arthritis.

Use of the compounds as above for the preparation of a medicament for the treatment and prophylaxis of cancer diseases, inflammatory bowel disease or rheumatoid arthritis.

In a further embodiment, the present invention relates to a pharmaceutical formulation comprising at least one compound according to formula (I) and/or pharmaceutically usable derivatives, salts and regioisomers thereof, including mixtures thereof in all ratios, and at least one further active ingredient.

The present invention further provides a pharmaceutical composition comprising at least one compound according to formula (I) and/or pharmaceutically usable derivatives, salts and regioisomers thereof, including mixtures thereof in all ratios, eventually one further active ingredient, and excipients.

The term "pharmaceutically acceptable salt" or "pharmaceutically acceptable derivatives" is taken to mean an active ingredient, which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The term "regioisomer" or "regioisomers" refers to the positional isomers, which is a category of structural isomers, wherein the position or the substituent changes position on the parent structure. Herein the term regioisomer without departing from the scope of compound of formula (I) inherently includes all regioisomers either as a pure regioisomer or mixture of two or more regioisomers thereof. Since the pharmaceutical activity of the regioisomers of the compounds of the present invention may differ, it may be desirable to use the regioisomers. In these cases the regioisomers can be separated at any of the possible stage either as an intermediate or as an end product by the process well known to the person skilled in the art or even employed as such in the synthesis. The regioisomers of the compounds of formula (I) refers to the following structures

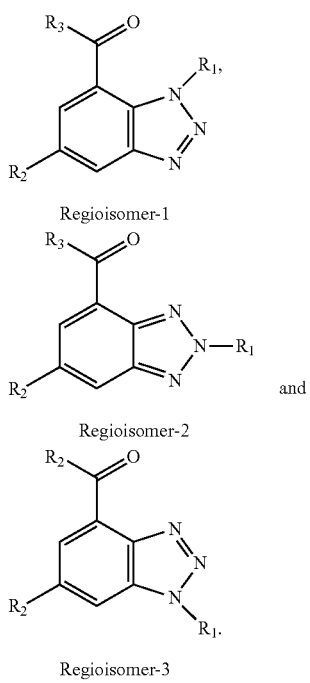

Regioisomer-1

Regioisomer-2 and

Regioisomer-3

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

For example, in the case of oral administration as tablet or capsule, the active-ingredient component can be combined with an oral, non-toxic and pharmaceutically acceptable inert excipient, such as, for example, ethanol, glycerol, water and the like.

Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

New trisubstituted benzotriazole derivatives of formula (I) and its pharmaceutically acceptable salts and physiologically functional derivatives thereof and the other active ingredients can also be administered in the form of liposome delivery systems, such as, for example, small unilamellar vesicles, large unilamellar vesicles and multilamellar vesicles. Liposomes can be formed from suitable lipids or phospholipids or both, such as, for example, cholesterol, stearylamine or phosphatidylcholines or the like.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations. Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I) and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In yet another embodiment, the present invention relates to a method for treating a cancer in a subject in need of such treatment comprising the step of administering to the subject one or more times a therapeutically effective amount of at least one compound or pharmaceutically acceptable salt thereof disclosed herein.

In yet another embodiment, the present invention relates to a method for inhibiting growth and/or metastasis of tumor cells in a subject, comprising the step of administering to the subject one or more times a therapeutically effective amount of at least one compound or pharmaceutically acceptable salt thereof as disclosed herein.

In yet another embodiment, the present invention relates to a method for inhibiting a dihydrorotate oxygenase enzyme activity in a tumor cell, comprising the step of contacting the tumor cell one or more times with a therapeutically effective amount of at least one compound or pharmaceutically acceptable salt thereof as disclosed herein. In this embodiment the tumor cells are contacted in vivo, ex vivo or in vitro.

The compounds, pharmaceutically acceptable salts thereof and pharmaceutical formulations and compositions disclosed herein are useful for treating cancer in a subject in need of such treatment. Concomitantly, tumor cell growth and/or metastasis or a dihydrorotate oxygenase enzyme activity therein may be inhibited. The compounds and pharmaceutical composition may be administered one or more times to achieve a therapeutic effect. As is known in the art, the skilled person is well able to determine dose, dosage regimens and routes of administration depending on the condition to be treated and the subject requiring treatment. Representative examples of a cancer include hematological malignancies such as, but not limited to, acute myeloid leukemia, multiple myeloma, B-prolymphocytic leukemia, acute lymphoblastic leukemia, and chronic lymphocytic leukemia. Representative examples of a cancer include lymphomas such as, but not limited to, Hodgkin's disease, non-Hodgkin's lymphoma, follicular lymphoma, diffuse large B cell lymphoma, anaplastic large cell lymphoma, and mantle cell lymphoma. Representative examples of a cancer include a solid cancer such as, but not limited to, lung cancer, breast cancer, triple negative breast cancer, melanoma, glioblastoma, prostate cancer, colon cancer, pancreatic cancer, bone cancer, cancer of the head or neck, skin cancer, cutaneous or intraocular malignant endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumours of childhood, lymphocytic lymphoma cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and PTEN mutant cancers.

In a further aspect, the present invention relates to a process for preparing trisubstituted benzotriazole derivatives of formula (I).

The dihydroorotate dehydrogenase inhibitors according to formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. Moreover, by utilizing the procedures described in detail, one of ordinary skill in the art can prepare additional compounds of the present invention claimed herein. All temperatures are in degrees Celsius (° C.) unless otherwise noted.

In a further aspect, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Isotopically labeled compounds of the present inventions can generally be prepared by following procedures analogous to those disclosed in the Schemes and/or in the Examples herein below, by substituting an isotopically labeled reagent for a non-isotopically labeled reagent.

The following abbreviations refer respectively to the definitions below:

AcOH (Acetic acid), ACN (Acetonitrile), ATP (Adenoside Triphosphate), BSA (Bovine Serum Albumin), CHCl$_3$ (Chloroform), Cs$_2$CO$_3$ (Cesium carbonate), DCM (Dichloromethane), DIPEA (di-isopropyl ethylamine), DMSO (Dimethyl Sulfoxide), DMF (N,N-Dimethylformamide), EDCI.HCl (1-Ethyl-3-(3-dimethylaminopropyl)carbodiimide hydrochloride), Et$_3$N (Triethylamine), EtOAc (Ethyl acetate), EtOH (Ethanol), HOBT (Hydroxybenzotriazole), HCl (Hydrogen chloride), K$_2$CO$_3$ (Potassium Carbonate), KOAc (Potassium acetate), min (minute), MeOH (Methanol), MeI (Methyl Iodide), MgSO$_4$ (Magnesium sulfate), NH$_4$Cl (Ammonium chloride), NH$_4$(CO$_3$)$_2$ (ammonium carbonate), Pd(dppf)$_2$Cl$_2$ ([1,1-bis(diphenylphosphino)-ferrocene] dichloropalladium (II)), NaH (Sodium hydride), NaNO$_2$ (Sodium nitrite), NaHCO$_3$ (Sodium bicarbonate), PetEther (Petroleum ether), PBS (Phosphate Buffered Saline), RT-room temperature (25° C.-35° C.), TEA (Triethyl amine), TFA (Trifluoroacetic acid), THF (Tetrahydrofuran), t-BuOK (Potassium tert-butoxide), TMSI (Trimethylsilyl iodide), TLC (Thin Layer Chromatography), H$_2$O—Water; mL—Milli Liter; hr/h—Hour; N—Normality; M—Molarity; s—Singlet; d—Doublet; t—Triplet; m—Multiplet; $^1$HNMR—Proton nuclear magnetic resonance; MS—Mass spectroscopy; LC—Liquid chromatography; HPLC—High Performance Liquid Chromatography, J—Coupling Constant; $^1$H—Proton; MHz—Mega Hertz (frequency); Hz—Hertz; ppm—Parts per million; bs—Broad singlet; ES—Electro spray; Conc.—Concentrated; g—Gram; mmol or mM—Milli molar; μM—Micro molar; nM—Nano molar; UV—Ultraviolet; ° C.—degree Celsius, M$^+$-Molecular ion, %—Percentage; μ—Micron; and δ—Delta; anh.—Anhydrous; pH—potential of Hydrogen;

Another embodiment of the present invention provides methods useful for making the compounds of formula (I) are set forth in the Examples below and generalized in Scheme-I. One of skill in the art will recognize that Scheme I can be adapted to produce the compounds of formula (I) and pharmaceutically accepted salts of compounds of formula (I) according to the present invention. Wherein all symbols/variables are as defined earlier unless otherwise stated. The process is represented by Scheme-I:

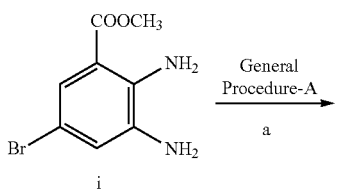

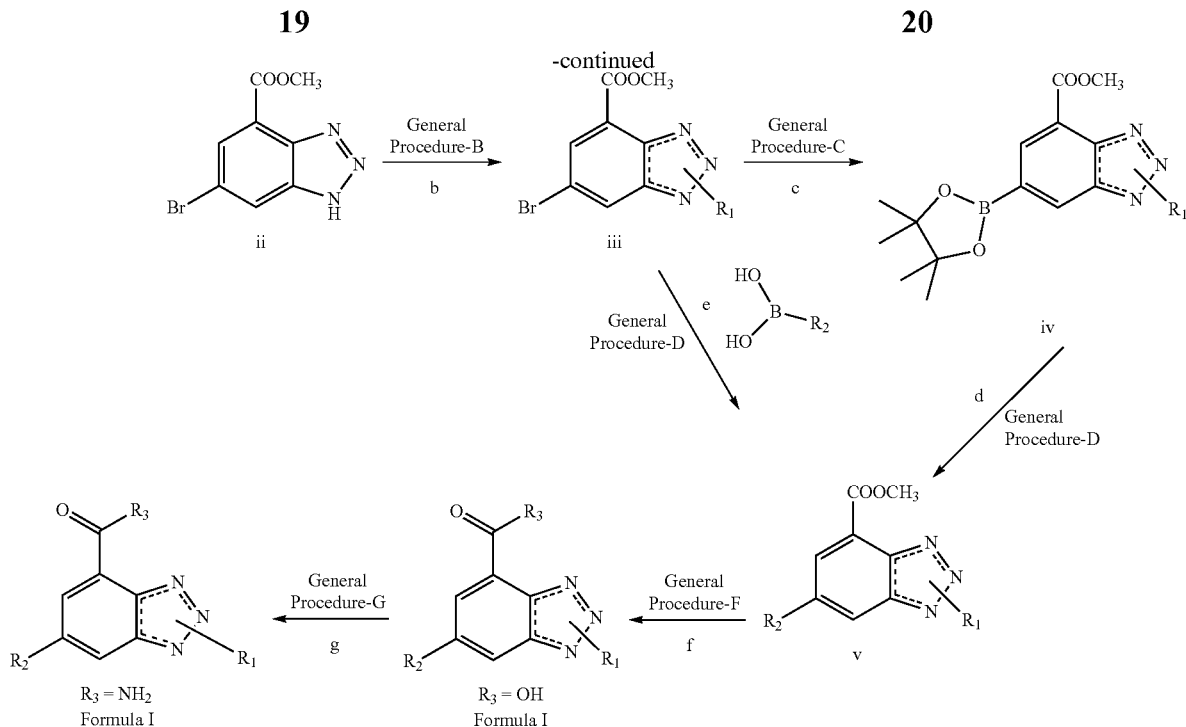

Compounds of the invention may be prepared using the synthetic transformations illustrated in Scheme-I. Starting materials are commercially available, may be prepared by the procedures described herein, by literature procedures, or by procedures that would be well known to one skilled in the art of organic chemistry. Starting material 5-substituted methyl 2,3-diamino-benzoate is prepared by the procedures described in WO 2010115736A2.

Step-a: Compound-i is reacted with sodium nitrite in acidic medium using General Procedure-A to afford the compound-ii.

Step-b: Compound-ii is further subjected to N-alkylation using methyl iodide in basic conditions such as those described in General Procedure-B to afford the compounds of formula-iii.

Step-c: The compounds of formula-iii are reacted with bispinacolate diboran in basic medium in presence of suitable palladium catalyst using General Procedure-C to afford the compounds of formula-iv.

Step-d: The compounds of formula-iv treated with substituted aryl halide in presence of suitable palladium catalyst using the conditions such as those described in General Procedure-D to afford the compounds of formula-v.

Step-e: Alternatively the compounds of formula-v can be prepared from the compounds of formula-iii by using appropriate boronic acids, at suitable conditions such as those described in General Procedure-D.

Step-f: The resultant compounds of formula-v under goes ester hydrolysis under basic conditions such as those described in General Procedure-F to afford compounds of formula (I) (wherein $R_3$=OH).

Step-g: Carboxylic acids of formula (I) was treated with ammonium chloride using the conditions that are described in General procedure-G to afford the respective compounds of formula (I) (wherein $R_3$=$NH_2$).

If the above set of general synthetic methods is not applicable to obtain compounds according to formula (I) and/or necessary intermediates for the synthesis of compounds of formula (I), suitable methods of preparation known by a person skilled in the art should be used. In general, the synthesis pathways for any individual compound of formula (I) will depend on the specific substituents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I) with a suitable base. Both types of salts may be formed or interconverted using ion-exchange resin techniques.

Although the invention is illustrated by certain of the following examples, it is not to be construed as being limited thereby; but rather, the invention encompasses the generic area as hereinbefore disclosed. Various modifications and embodiments can be made without departing from the spirit and scope thereof.

EXAMPLES

General:

The MS data provided in the examples described below were obtained as followed: Mass spectrum: LC/MS Waters ZMD (ESI) or a Waters Acquity SQD (ESI).

The NMR data provided in the examples described below were obtained as followed: $^1$H-NMR: Bruker DPX-300MHz or a Bruker DPX 400 MHz.

The HPLC data provided in the examples described below were obtained as followed.

Condition A: Column Waters Xbridge™ $C_8$ 50 mm×4.6 mm at a flow of 2 mL/min; 8 min gradient from 0.1% TFA in $H_2O$ to 0.07% TFA in $CH_3CN$.

Condition B: C18 BDS (4.6×250) mm, SC \244 at a flow of 0.7 mL/min; 10 min gradient from 0.1% TFA in $H_2O$ to $CH_3CN$.

Preparative HPLC conditions: Column—Zorbax Eclipse XDB C18 PrepHT (150×21.2 mm, 5μ); Mobile Phase: (A) 0.01% TFA or 0.1% TFA; (B) ACN or ACN: MeOH (1:1); Flow: 20 ml/min.

Preparative HPLC purifications were performed with a mass directed autopurification Fractionlynx from Waters equipped with a Sunfire Prep C18 OBD column 19×100 mm 5 μm, unless otherwise reported. All HPLC purifications were performed with a gradient of $ACN/H_2O$ or $ACN/H_2O/HCOOH$ (0.1%).

The compounds of invention have been named according to the standards used in the programACD/Name Batch from "Advanced Chemistry Development Inc., ACD/Labs (7.00 Release)". Product version: 7.10 build: 15 Sep. 2003.

The procedure for the compounds of formula (I) are detailed herein below the general procedures including the general synthesis of various intermediates involved in process of manufacture of the compounds according to the present invention.

General Procedure-A: Preparation of Substituted [1,2,3] benzotriazoles

To a flask containing 6-substituted or substituted diamino ester (1-3 equiv) in acetic acid is stirred for 10-20 min preferably 10 min followed by the addition of (sodium nitrite, potassium nitrite preferably sodium nitrite) (2.5-3.5 preferably 2.5 equiv) in water. The reaction mixture stirred for 1-2 h. preferably 1 h at RT. The separated solid is collected by filtration and dried under vacuum to obtain the target products.

Illustrative Example of General Procedure-A:
Preparation # A.1: Synthesis of methyl 6-bromo-1H-benzo[d][1,2,3]triazole-4-carboxylate:

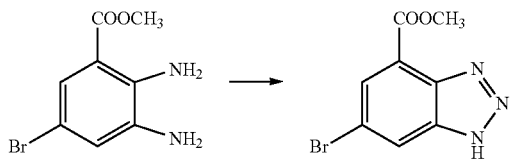 [SMILES: COC(=O)c1cc(Br)cc(N)c1N ; COC(=O)c1cc(Br)cc2[nH]nnc12]

A solution of methyl 2,3-diamino-5-bromobenzoate (1.0 g, 4.08 mmol) (Ref: WO2010/115736 A2) in acetic acid (15 mL) was stirred for 10 min at RT. Sodium nitrite (0.309 g, 4.48 mmol) in water (2 mL) was added and the reaction mixture stirred for about 30 min at RT. The precipitated solid was filtered, washed with water and dried under vacuum to afford desired product (0.8 g, 77%); $^1H$ NMR (400 MHz, DMSO-d6): δ 16.19 (s, 1H), 8.70 (s, 1H), 8.14 (s, 1H), 3.99 (s, 3H) and LC-MS m/z: 258 (M+H)$^+$.

General Procedure-B: N-alkylation of Substituted benzotrizoles

To a stirred solution of substituted Benzotriazoles-carboxylate derivative (1 equiv) in an organic solvent (such as DMF, THF, Dioxane preferably DMF) is added a suitable base (such as $K_2CO_3$, $CS_2CO_3$, NaH etc. preferably $K_2CO_3$ 2 to 5 equivalents preferably 2. equiv) followed by alkyl halide (2 to 5 equiv, preferably 3 equiv). The reaction mixture stirred RT for about 1 to 10 h (preferably 3 h). The reaction mixture is poured into ice cold water and the separated solid is collected by filtration and dried under vacuum. The regioisomers were separated by column chromatography to obtain the desired products.

Illustrative Example of General Procedure-B:
Preparation # B.1: Synthesis of methyl 5-bromo-1-methyl-1H-benzo[d][1,2,3]triazole-7-carboxylate, methyl 6-bromo-2-methyl-2H-benzo[d][1,2,3]triazole-4-carboxylate and methyl 6-bromo-1-methyl-1H-benzo[d][1,2,3] triazole-4-carboxylate

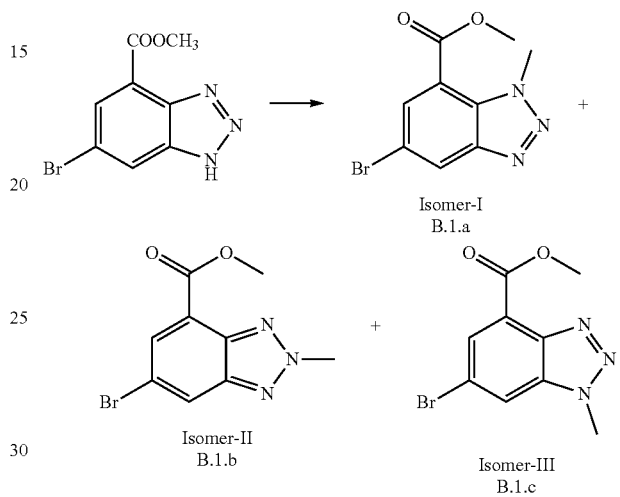

To a stirred solution of methyl 6-bromo-1H-benzo[d][1,2,3]triazole-4-carboxylate (4.5 g, 17.5 mmol, preparation # A.1) in DMF (25 mL) was added potassium carbonate (4.85 g, 35.15 mmol) followed by methyl iodide (7.48 g, 52.73 mmol). The reaction mixture was stirred at RT for 1 h. The reaction mixture was quenched with ice cold water (100 mL) and the separated solid was collected by filtration, dried under vacuum. The obtained crude compound was purified by column chromatography over silica gel (100-200 mesh) using 10% ethyl acetate in hexane to get the Isomer-I (B.1.a) (1.9 g); $^1H$ NMR (400 MHz, CDCl$_3$) δ 8.40 (s, 1H), 8.22 (s, 1H), 4.57 (s, 3H), 4.01 (s, 3H) and LC-MS m/z: 272 (M+2)$^+$; 15-20% ethyl acetate in hexane to get the Isomer-II (B.1.b) (1.4 g); $^1H$ NMR (400 MHz, CDCl$_3$) δ 8.26 (s, 1H), 8.23 (s, 1H), 4.58 (s, 3H), 4.04 (s, 3H) and LC-MS m/z: 272.0 (M+2)$^+$; 20-25% ethyl acetate in hexane to get the Isomer-III (B.1.c) (1.0 g); $^1H$ NMR (400 MHz, DMSO-d$_6$): δ 8.67 (s, 1H), 8.13 (s, 1H), 4.45 (s, 3H), 3.96 (s, 3H) and LC-MS m/z: 272.0 (M+2)$^+$.

General Procedure-C: Preparation of boronic ester

A mixture of aryl halo derivative (1.0 to 3.0 equiv, preferably 1.0 equiv), suitable inorganic base (such as KOAC or $Na_2CO_3$ or $K_2CO_3$ or $Cs_2CO_3$ preferably KOAC), bispinacolate diborane (1.0 to 3.0 equiv, preferably 1.1 equiv) in dioxane is degased with nitrogen for about 10 to 15 min and added [1, 1-bis (diphenylphosphino)-ferrocene] dichloropalladium (II) (0.001 to 0.010 equiv, preferably 0.05 equiv). The reaction mixture is stirred at reflux temperature under nitrogen for about 3 h to 12 h (preferably about 6 h). The reaction mixture is cooled to RT and evaporated to dryness under reduced pressure. The residue obtained is re-dissolved in EtOAc, washed successively with water and brine solution. The organic solution is dried over $Na_2SO_4$, filtered and concentrated under reduced pressure. The product is purified by crystallization or trituration from an appropriate solvent or solvents or by preparative HPLC or flash chromatography.

Illustrative Example of General Procedure-C:

Preparation # C.1: Synthesis of methyl 1-methyl-5-(4,4,5, 5-tetramethyl-1,3,2-dioxaborolan-2-yl)-1H-benzo[d][1,2,3] triazole-7-carboxylate

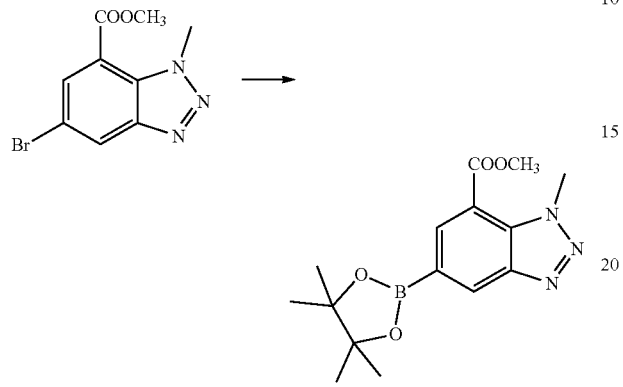

A mixture of methyl 5-bromo-1-methyl-1H-benzo [d][1, 2,3] triazole-7-carboxylate (1.0 g, 3.7 mmol, preparation # B.1.a), potassium acetate (0.627 g, 5.92 mmol), bispinacolate diborane (0.93 g, 3.7 mmol) in dioxane (60 mL) was degased with nitrogen for about 15 min and added [1, 1-bis (diphenylphosphino)-ferrocene]dichloropalladium(II) (0.151 g, 0.018 mmol). The reaction mixture was stirred at reflux temperature for 6 h under nitrogen. The reaction mixture was cooled to RT and evaporated to dryness under reduced pressure. The residue obtained was re-dissolved in EtOAc, washed successively with water and brine solution and concentrated. The obtained crude compound was purified by column chromatography over silica gel (60-120 mesh) using 30% ethyl acetate in hexane to get the desired product (0.9 g, 77%); $^1$H NMR (400 MHz, DMSO-d6): δ 8.46 (s, 1H), 8.31 (s, 1H), 4.59 (s, 3H), 3.94 (s, 3H), 1.35 (s, 12H) and LC-MS m/z=318.2 (M+H)$^+$.

Other compounds synthesized using General procedure C are described in Table C.1

General Procedure-D: Suzuki Reaction

A mixture of acetonitrile and water (8:2) is degased with nitrogen for about 10 to 15 min then added suitable base (such as $Na_2CO_3$ or $K_2CO_3$ or $Cs_2CO_3$ preferably $Na_2CO_3$) followed by aryl bromo derivative (1.0 to 3.0 equiv, preferably 1.0 equiv) and appropriate boronic acid (1.0 to 3.0 equiv, preferably 1.5 equiv). The reaction mixture is again degassed for 15 min and finally added [1, 1-bis(diphenylphosphino)-ferrocene] dichloropalladium(II) (0.001 to 0.010 equiv, preferably 0.05 equiv) is added. The reaction mixture is stirred at reflux temperature under nitrogen for about 3 h to 12 h (preferably about 4 h). The reaction mixture is cooled to RT and evaporated to dryness under reduced pressure. The obtained residue is re-dissolved in EtOAc, washed successively with water and brine solution. The organic solution is dried over $Na_2SO_4$, filtered and concentrated under reduced pressure. The product is purified by crystallization or trituration from an appropriate solvent or solvents or by preparative HPLC or flash chromatography.

Illustrative Example of General Procedure-D:

Preparation # D.1: Synthesis of methyl 1-methyl-5-(2'-methyl-[1,1'-biphenyl]-4-yl)-1H-benzo[d][1,2,3] triazole-7-carboxylate

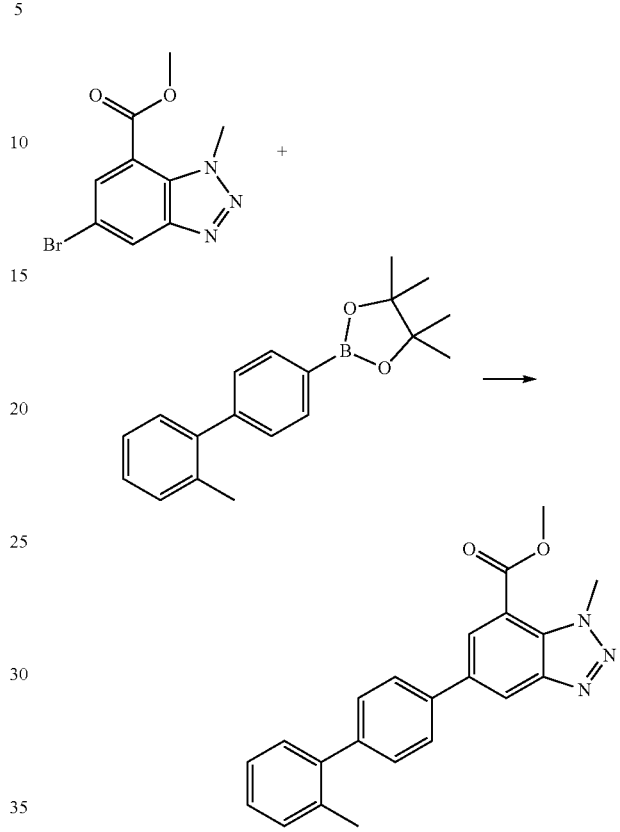

A mixture of acetonitrile (80 mL) and water (15 mL) was degassed with nitrogen for 10 min. Sodium carbonate (2.74 g, 25.9 mmol) was added followed by methyl 5-bromo-1-methyl-1H-benzo[d][1,2,3]triazole-7-carboxylate (3.5 g, 12.9 mmol) and 4,4,5,5-tetramethyl-2-(2'-methyl-[1,1'-biphenyl]-4-yl)-1,3,2-dioxaborolane (3.81 g, 12.0 mmol) (C.1.5). The reaction mixture was again degassed for 15 min. Finally [1,1-bis(diphenylphosphino)-ferrocene]dichloropalladium(II) (0.526 g, 0.64 mmol) was added. The reaction mixture was stirred at reflux temperature for 5 h under nitrogen. The reaction mixture was cooled to RT and evaporated to dryness under reduced pressure. The obtained residue was re-dissolved in EtOAc, washed successively with water and brine solution and concentrated. The obtained crude compound was purified by column chromatography over silica gel (60-120 mesh) using 30% ethyl acetate in hexane to get the desired product (3.6 g, 77%); $^1$H NMR (400 MHz, CDCl$_3$): δ 8.52 (s, 1H), 8.31 (s, 1H), 7.76-7.74 (d, J=8.0 Hz, 2H), 7.48-7.46 (d, J=7.6, 2H), 7.31-7.28 (m, 4H), 4.63 (s, 3H), 4.08 (s, 3H), 2.34 (s, 3H) and LC-MS m/z=358.2 (M+H)$^+$.

Other compounds synthesized using General procedure D are described in Table D.1.

General Procedure-E: Reductive Amination

A mixture of appropriate aldehyde and amine in organic solvent (such as DCM, THF, ACN, DMF, DCE, or Dioxane) is stirred at room temperature for 30 min to 4 hrs. The resulting reaction mixture is cooled to 0° C. and added reducing agent such as sodium triacetoxyborohydride in small portions followed by catalytic amount of acetic acid.

The resulting reaction mixture is stirred at room temperature for 2-4 hrs. The progress of the reaction is monitored by TLC, and the reaction mixture is quenched with an aq. solution of sodium bicarbonate. Further it is extracted with ethyl acetate, the combined organic layers are dried over sodium sulphate and concentrated under vacuum to afford the target compound. Optionally, the target compound can be purified by crystallization or trituration from an appropriate solvent or solvents, or by preparative HPLC or flash chromatography.

Illustrative Example of General Procedure-E:

Preparation #E.1: Synthesis of methyl 1-methyl-5-(2'-(morpholinomethyl)-[1,1'-biphenyl]-4-yl)-1H-benzo[d][1,2,3]triazole- 7-carboxylate

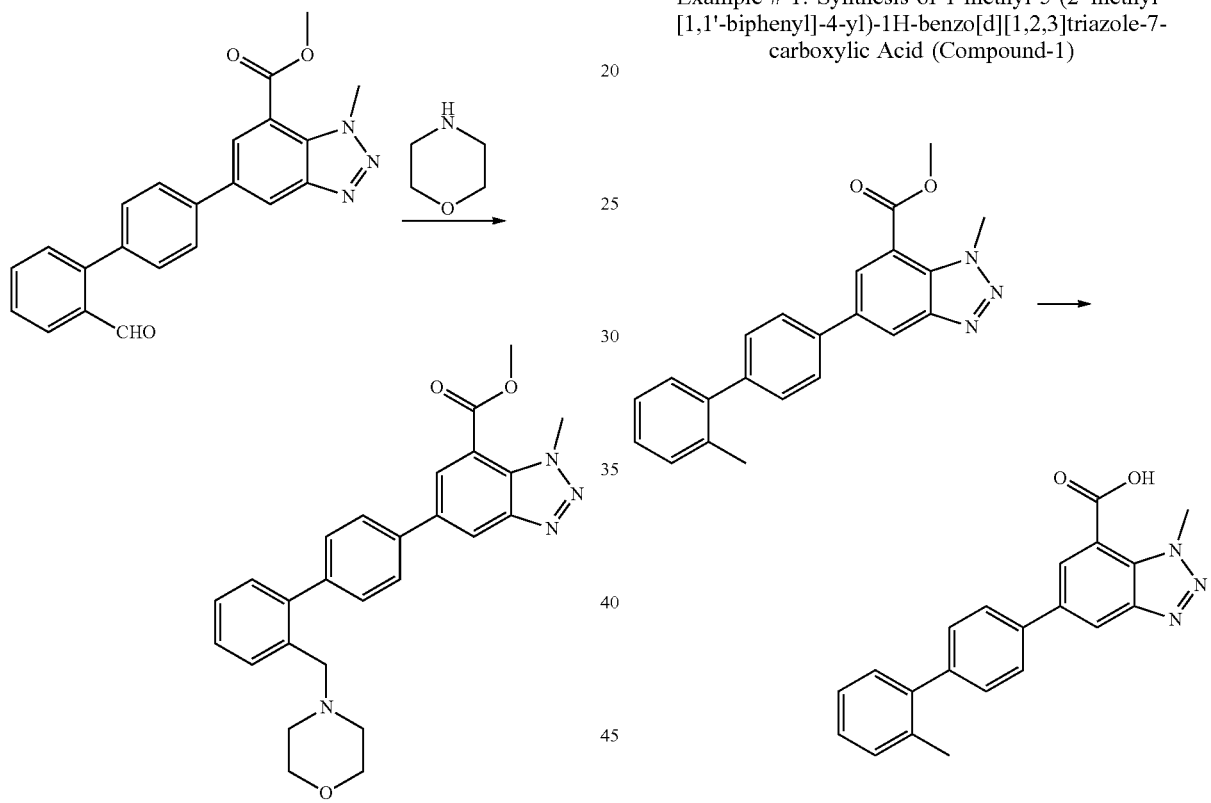

A solution of methyl 5-(2'-formyl-[1,1'-biphenyl]-4-yl)-1-methyl-1H-benzo[d][1,2,3]triazole-7-carboxylate (0.300 g, 0.8 mmol, D.1.8) and morpholine (0.070 g, 0.8 mmol) in DCE (15 mL) was stirred for 30 min at room temperature. The reaction mixture was cooled to 0° C., added sodium triacetoxy borohydride (0.342 g, 1.6 mmol) followed by acetic acid (0.2 mL). The reaction mixture was stirred for 2 h at room temperature. The reaction mixture was quenched with an aq. solution of sodium bicarbonate (50 mL). It was extracted with ethyl acetate (3×50 mL), combined organic layers were dried over sodium sulphate and concentrated under reduced pressure. The obtained crude was taken to next step without purification (0.200 g); $^1$H NMR (400 MHz, DMSO-d$_6$): δ 8.69 (s, 1H), 8.696 (s, 1H), 8.424-8.422 (d, J=8 Hz, 2H), 7.912-7.891 (d, J=8 Hz, 2H), 7.607 (m, 1H), 7.531-7.324 (m, 3H), 4.50 (s, 3H), 4.0 (s, 3H), 3.560 (m, 4H), 3.55 (s, 2H), 3.308 (m, 4H) and LC-MS m/z=443.3 (M+H)$^+$.

General Procedure-F: ester hydrolysis

To a flask containing an appropriate alkyl ester in an aqueous organic solvent (such as THF or methanol, 1,4 Dioxane preferably 1,4 Dioxane) is added 1.5 equiv. of aqueous sodium hydroxide solution and the reaction mixture is refluxed for 1-8 h. (preferably 4 h). Completion of the reaction is monitored by TLC. Excess solvent is removed under vacuum and the solution is acidified with 10% HCl solution. The separated solid is collected by filtration and dried under vacuum to obtain the target carboxylic acid derivative. Optionally, the target compound can be purified by crystallization or trituration from an appropriate solvent or solvents, or by preparative HPLC or flash chromatography.

Illustrative Example of General Procedure-F:

Example # 1: Synthesis of 1-methyl-5-(2'-methyl-[1,1'-biphenyl]-4-yl)-1H-benzo[d][1,2,3]triazole-7-carboxylic Acid (Compound-1)

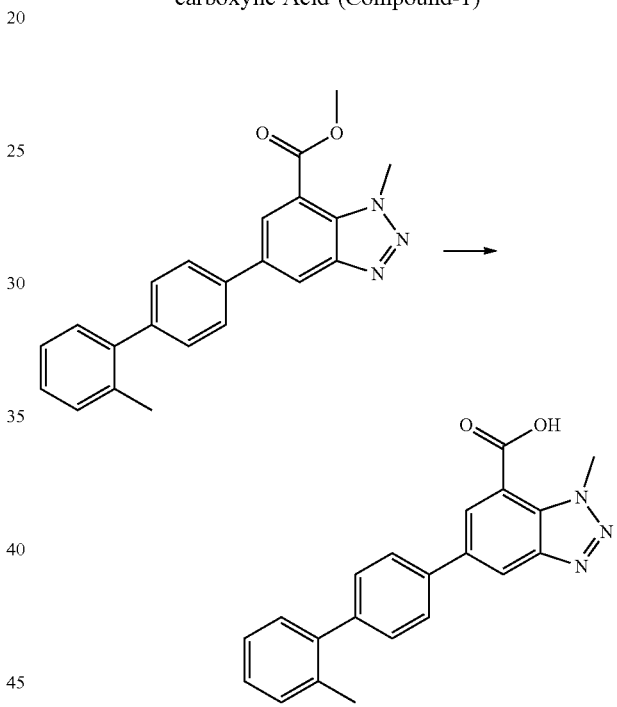

To a stirred solution of methyl 1-methyl-5-(2'-methyl-[1,1'-biphenyl]-4-yl)-1H-benzo[d][1,2,3]triazole-7-carboxylate (1.2 g, 3.361 mmol, D.1) in 1,4 Dioxane (15 mL) was added aq. 2N NaOH (15 mL). The reaction mixture was refluxed for 4 h. After the completion of the reaction, the reaction mixture was cooled to room temperature, excess solvent was removed under reduced pressure and the solution was acidified with 10% HCl solution (pH-2). The separated solid is collected by filtration and dried under vacuum to get the titled compound as an off white solid (1.1 g, 95%); $^1$H NMR (400 MHz, DMSO-d6): δ 13.35 (bs, 1H), 8.52 (s, 1H), 8.38 (s, 1H), 7.89-7.87 (d, J=8.0 Hz, 2H), 7.51-7.49 (d, J=8.4 Hz, 2H), 7.32-7.25 (m, 4H), 4.58 (s, 3H) 2.30 (s, 3H) and LC-MS m/z =344.1 (M+H)$^+$.

General Procedure-G: Amide Formation

To a flask containing appropriate carboxylic acid derivative (1.0 equiv) in an organic solvent (such as DMF, THF or CH$_2$Cl$_2$) is added EDCI.HCl (1.5 equiv), HOBT (1.5 equiv) and N-ethyl-N-isopropylpropan-2-amine (3 equiv). After stirring for about 10 min at approximately 25° C., the appropriate amine (1.5 equiv) is added and the reaction is stirred for an additional 8-12 h (preferably 12 h.). The separated solid upon addition of water is collected by filtration and dried under vacuum to obtain the amide derivative. Optionally, the obtained compound can be purified by crystallization or trituration from an appropriate solvent or solvents, or by preparative HPLC or flash chromatography.

Illustrative Example of General Procedure-G:

Example # 2: Synthesis of 1-methyl-5-(2'-methyl-[1,1'-biphenyl]-4-yl)-1H-benzo[d] [1,2,3]triazole-7-carboxamide (Compound-2)

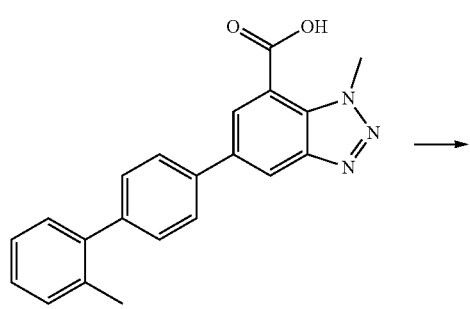

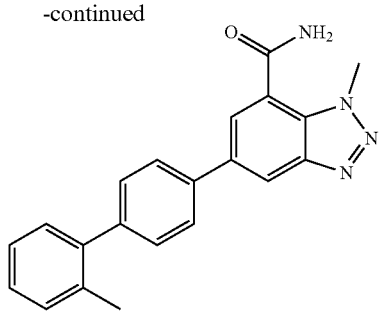

To a flask containing a 1-methyl-5-(2'-methyl-[1,1'-biphenyl] -4-yl)-1H-benzo[d][1,2,3]triazole-7-carboxylic acid (0.150 g, 0.43 mmol, Compound-1) in DMF (3 mL) was added EDCI.HCl (0.100 g, 0.52 mmol), HOBT (0.070 g, 0.52 mmol) and N-ethyl-N-isopropylpropan-2-amine (0.168 g, 1.31 mmol) .The mixture was stirred at about 25° C. for approximately 10 min and was added ammonium chloride (0.070 g, 1.31 mmol). The reaction was then stirred for about additional 12 h and quenched with water (50 mL). The separated solid was collected by filtration and dried under vacuum to get the desired compound as an off white solid (0.08 g, 53%); $^1$H NMR (400 MHz, DMSO-d6): δ 8.47 (s, 1H), 8.37 (s, 1H), 8.05 (s, 1H), 8.00 (s, 1H), 7.90-7.88 (d, J=8.0 Hz, 2H), 7.51-7.49 (d, J=7.6 Hz, 2H), 7.35-7.27 (m, 4H), 4.61 (s, 3H), 2.30 (s, 3H) and LC-MS m/z=343.2 (M+H)$^+$.

The below intermediates were prepared by procedure similar to the one described in General procedure-C with appropriate variations in reactants, quantities of reagents and reaction conditions. The physiochemical characteristics of the compounds are summarized herein below Table C.1.

TABLE C.1.

| Int No. | Reactant/Source | Intermediate Structure | Analytical data |
|---|---|---|---|
| C.1.1 | | | $^1$H NMR (400 MHz, DMSO-d6): δ 8.46 (s, 1H), 8.31 (s, 1H), 4.59 (s, 3H), 3.94 (s, 3H), 1.35 (s, 12H) and LC-MS m/z = 318.2 (M + H)$^+$. |
| C.1.2 | | | $^1$H NMR (400 MHz, DMSO-d6): δ 7.80-7.78 (d, J = 8 Hz, 2H), 7.27-7.25 (d, J = 8 Hz, 2H), 5.80 (m, 2H), 1.96 (s, 6H), 1.31 (s, 12H) and LC-MS m/z = 298.2 (M + H)$^+$. |

TABLE C.1.-continued

| Int No. | Reactant/ Source | Intermediate Structure | Analytical data |
|---|---|---|---|
| C.1.3 | 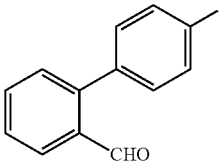 JOC, 2008, vol. 73, #14 p. 5558-65 | 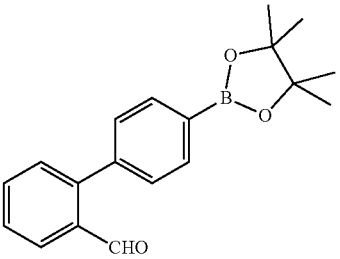 | $^1$H NMR (400 MHz, DMSO-d6): δ 9.88 (s, 1H), 7.94 (d, J = 7.2 Hz, 1H), 7.81-7.75 (m, 3H), 7.63-7.45 (m, 4H), 1.32 (s, 12H) and LC-MS m/z = 298.2 (M + H)$^+$. |
| C.1.4 | 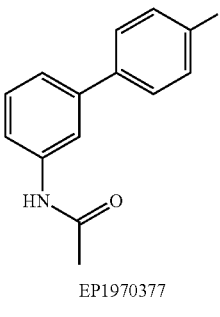 EP1970377 | 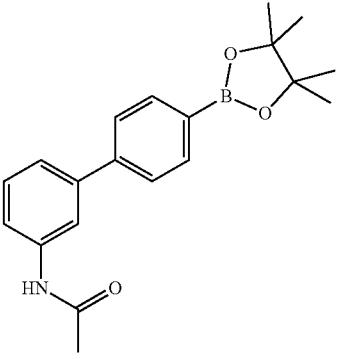 [SMILES: CC(=O)Nc1cccc(-c2ccc(B3OC(C)(C)C(C)(C)O3)cc2)c1] | $^1$H NMR (400 MHz, DMSO-d6): δ 10.04 (s, 1H), 7.92-7.91 (d, J = 4 Hz, 1H), 7.83-7.58 (m, 4H), 7.41-7.33 (m, 2H), 2.06 (s, 3H), 1.31 (s, 12H) and LC-MS m/z = 338.2 (M + H)$^+$. |
| C.1.5 | 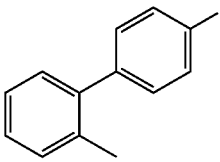 Synlett, 2005, #11, p. 1775-78. | 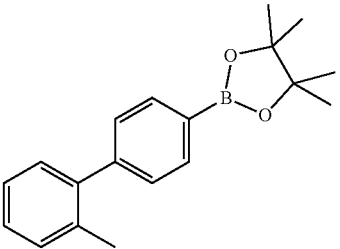 [SMILES: Cc1ccccc1-c1ccc(B2OC(C)(C)C(C)(C)O2)cc1] | $^1$H NMR (400 MHz, CDCl$_3$): δ 7.87-7.85 (d, J = 8 Hz, 2H), 7.35-7.33 (d, J = 8 Hz, 2H), 7.26-7.24 (m, 4H), 2.26 (s, 3H), 1.36 (s, 12H) and LC-MS m/z = 295.2 (M + H)$^+$. |

The below intermediates were prepared by procedure similar to the one described in General procedure-D with appropriate variations in reactants, quantities of reagents and reaction conditions. The physiochemical characteristics of the compounds are summarized herein below table-D.1.

TABLE D.1.

| Int No. | Reactant/Source | Intermediate Structure | Analytical data |
|---|---|---|---|
| D.1.1 | 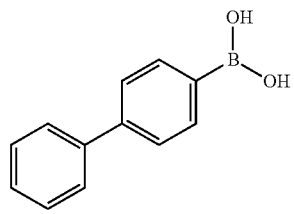 [SMILES: OB(O)c1ccc(-c2ccccc2)cc1] | 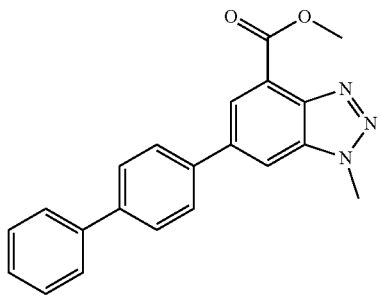 [SMILES: COC(=O)c1cc(-c2ccc(-c3ccccc3)cc2)cc2c1nnn2C] | $^1$H NMR (400 MHz, DMSO-d6): δ 8.50 (s, 1H), 8.30 (s, 1H), 7.79-7.65 (m, 6H), 7.48-7.38 (m, 3H), 4.62 (s, 3H), 4.08 (s, 3H) and LC-MS m/z = 344 (M + H)$^+$. |

TABLE D.1.-continued

| Int No. | Reactant/Source | Intermediate Structure | Analytical data |
|---|---|---|---|
| D.1.2 | [4-phenylphenyl]boronic acid | methyl 1-methyl-6-([1,1'-biphenyl]-4-yl)-1H-benzo[d][1,2,3]triazole-7-carboxylate | $^1$H NMR (400 MHz, CDCl$_3$): δ 8.48-8.46 (d, J = 8.8 Hz, 2H), 7.78-7.65 (m, 6H), 7.48-7.37 (m, 3H), 4.62 (s, 3H), 4.04 (s, 3H) and LC-MS m/z = 344 (M + H)$^+$. |
| D.1.3 | [4-phenylphenyl]boronic acid | methyl 2-methyl-5-([1,1'-biphenyl]-4-yl)-2H-benzo[d][1,2,3]triazole-4-carboxylate | LC-MS m/z = 344 (M + H)$^+$. |
| D.1.4 | [4-phenylphenyl]boronic acid | methyl 6-([1,1'-biphenyl]-4-yl)-1H-benzo[d][1,2,3]triazole-7-carboxylate | $^1$H NMR (400 MHz, DMSO-d6): δ 16.05 (s, 1H), 8.73 (s, 1H), 8.42 (s, 1H), 7.94-7.92 (d, J = 8 Hz, 2H), 7.84-7.82 (d, J = 8 Hz, 2H), 7.76-7.74 (m, 2H), 7.53-7.38 (m, 3H), 4.03 (s, 3H) and LC-MS m/z = 330.2 (M + H)$^+$. |
| D.1.5 | 2,5-dimethyl-1-(4-(4,4,5,5-tetramethyl-1,3,2-dioxaborolan-2-yl)phenyl)-1H-pyrrole | methyl 6-(4-(2,5-dimethyl-1H-pyrrol-1-yl)phenyl)-1-methyl-1H-benzo[d][1,2,3]triazole-7-carboxylate | $^1$H NMR (400 MHz, DMSO-d6): δ 8.69 (s, 1H), 8.41 (s, 1H), 7.96-7.94 (d, J = 8 Hz, 2H), 7.41-7.39 (d, J = 8 Hz, 2H), 5.8 (s, 2H), 4.50 (s, 3H), 4.00 (s, 3H), 2.02 (s, 6H) and LC-MS m/z = 361.2 (M + H)$^+$. |
| D.1.6 | 2,5-dimethyl-1-(4-(4,4,5,5-tetramethyl-1,3,2-dioxaborolan-2-yl)phenyl)-1H-pyrrole | methyl 5-(4-(2,5-dimethyl-1H-pyrrol-1-yl)phenyl)-2-methyl-2H-benzo[d][1,2,3]triazole-4-carboxylate | $^1$H NMR (400 MHz, DMSO-d6): δ 8.58 (s, 1H), 8.40 (s, 1H), 7.95-7.93 (d, J = 8 Hz, 2H), 7.41-7.39 (d, J = 8 Hz, 2H), 5.83 (s, 2H), 4.59 (s, 3H), 4.00 (s, 3H), 2.02 (s, 6H) and LC-MS m/z = 361.1 (M + H)$^+$. |

TABLE D.1.-continued

| Int No. | Reactant/Source | Intermediate Structure | Analytical data |
|---|---|---|---|
| D.1.7 | (4-(2,5-dimethyl-1H-pyrrol-1-yl)phenyl)boronic acid pinacol ester | methyl 6-(4-(2,5-dimethyl-1H-pyrrol-1-yl)phenyl)-1-methyl-1H-benzo[d][1,2,3]triazole-4-carboxylate | ¹H NMR (400 MHz, DMSO-d6): δ 8.57 (s, 1H), 8.39 (s, 1H), 7.95-7.93 (d, J = 8 Hz, 2H), 7.41-7.39 (d, J = 8 Hz, 2H), 5.83 (s, 2H), 4.59 (s, 3H), 4.00 (s, 3H), 2.02 (s, 6H) and LC-MS m/z = 361.2 (M + H)⁺. |
| D.1.8 | (3'-formyl-[1,1'-biphenyl]-4-yl)boronic acid | methyl 6-(3'-formyl-[1,1'-biphenyl]-4-yl)-1-methyl-1H-benzo[d][1,2,3]triazole-4-carboxylate | ¹H NMR (400 MHz, DMSO-d6): δ 10.13 (s, 1H), 8.71 (s, 1H), 8.41 (s, 1H), 8.29 (s, 1H), 8.12-8.10 (d, J = 8 Hz, 1H), 7.994-7.905 (m, 5H), 7.75-7.72 (m, 1H), 4.49 (s, 3H), 4.00 (s, 3H) and LC-MS m/z = 372.1 (M + H)⁺. |
| D.1.9 | (3'-formyl-[1,1'-biphenyl]-4-yl)boronic acid | methyl 6-(3'-formyl-[1,1'-biphenyl]-4-yl)-2-methyl-2H-benzo[d][1,2,3]triazole-4-carboxylate | ¹H NMR (400 MHz, DMSO-d6): δ 10.13 (s, 1H), 8.60 (s, 1H), 8.42 (s, 1H), 8.3 (s, 1H), 8.13-8.11 (d, J = 8 Hz, 1H), 7.99-7.92 (m, 5H), 7.76-7.72 (m, 1H), 4.60 (s, 3H), 4.01 (s, 3H) and LC-MS m/z = 372.2 (M + H)⁺. |
| D.1.10 | (3'-formyl-[1,1'-biphenyl]-4-yl)boronic acid | methyl 6-(3'-formyl-[1,1'-biphenyl]-4-yl)-3-methyl-3H-benzo[d][1,2,3]triazole-4-carboxylate | ¹H NMR (400 MHz, DMSO-d6): δ 10.14 (s, 1H), 8.57 (s, 1H), 8.32 (s, 1H), 8.31 (s, 1H), 8.14-8.12 (d, J = 8 Hz, 1H), 8.031-7.93 (m, 5H), 7.77-7.73 (m, 1H), 4.43 (s, 3H), 4.01 (s, 3H) and LC-MS m/z = 372.2 (M + H)⁺. |

TABLE D.1.-continued

| Int No. | Reactant/Source | Intermediate Structure | Analytical data |
|---|---|---|---|
| D.1.11 | (4'-formyl-[1,1'-biphenyl]-4-yl)boronic acid | methyl 5-(4'-formyl-[1,1'-biphenyl]-4-yl)-1-methyl-1H-benzo[d][1,2,3]triazole-4-carboxylate | $^1$H NMR (400 MHz, DMSO-d6): δ 10.08 (s, 1H), 8.72 (s, 1H), 8.42 (s, 1H), 8.04-7.92 (m, 8H), 4.49 (s, 3H), 4.00 (s, 3H) and LC-MS m/z = 372.1(M + H)$^+$. |
| D.1.12 | 2'-(4,4,5,5-tetramethyl-1,3,2-dioxaborolan-2-yl)-[1,1'-biphenyl]-2-carbaldehyde | methyl 5-(2'-formyl-[1,1'-biphenyl]-4-yl)-1-methyl-1H-benzo[d][1,2,3]triazole-7-carboxylate | $^1$H NMR (400 MHz, DMSO-d6): δ 9.98 (s, 1H), 8.73 (s, 1H), 7.99-7.97 (m, 3H), 7.82-7.80 (m, 1H), 7.784-7.61 (m, 4H), 4.50 (s, 3H), 4.00 (s, 3H) and LC-MS m/z = 372.1 (M + H)$^+$. |
| D.1.13 | 2'-(4,4,5,5-tetramethyl-1,3,2-dioxaborolan-2-yl)-[1,1'-biphenyl]-2-carbaldehyde | | $^1$H NMR (400 MHz, DMSO-d6): δ 9.98 (s, 1H), 8.61 (s, 1H), 8.43 (s, 1H), 7.98-7.96 (m, 3H), 7.80-7.79 (m, 1H), 7.64-7.59 (m, 4H), 4.60 (s, 3H), 3.98 (s, 3H) and LC-MS m/z = 372.2 (M + H)$^+$. |
| D.1.14 | 4-bromo-2,3,5,6-tetrafluoro-1,1'-biphenyl<br>Organic Letters, 2009, vol. 11, #15, p. 3346-49 | | $^1$H NMR (400 MHz, DMSO-d6): δ 8.30-8.28 (m, 2H), 7.54-7.50 (m, 5H), 4.65 (s, 3H), 4.07 (s, 3H) and LC-MS m/z = 416.1 (M + H)$^+$. |
| D.1.15 | 4-bromo-2,3,5,6-tetrafluoro-1,1'-biphenyl<br>Organic Letters, 2009, vol. 11, #15, p. 3346-49 | | LC-MS m/z = 416.1 (M + H)$^+$. |

TABLE D.1.-continued

| Int No. | Reactant/Source | Intermediate Structure | Analytical data |
|---|---|---|---|
| D.1.16 | 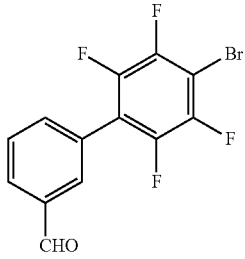 [SMILES: O=Cc1cccc(-c2c(F)c(F)c(Br)c(F)c2F)c1] | 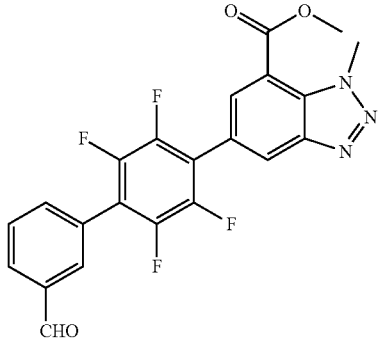 [SMILES: COC(=O)c1cc(-c2c(F)c(F)c(-c3cccc(C=O)c3)c(F)c2F)cc2nnn(C)c12] | $^1$H NMR (400 MHz, DMSO-d6): δ 10.12 (s, 1H), 8.67 (s, 1H), 8.26 (s, 1H), 8.13-8.11 (m, 2H), 7.96 -7.83 (m, 2H), 4.53 (s, 3H), 4.0 (s, 3H); LC-MS m/z = 444.1 (M + H)$^+$. |
| D.1.17 | 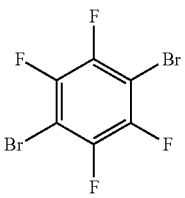 | 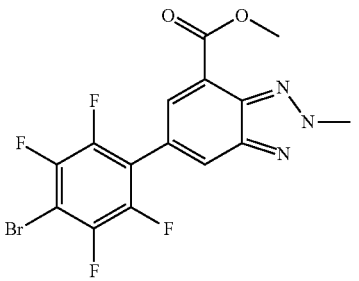 [SMILES: CN/N=C1\C(=N)C=C(c2c(F)c(F)c(Br)c(F)c2F)C=C1C(=O)OC] | $^1$H NMR (400 MHz, DMSO-d6): δ 8.52 (s, 1H), 8.37 (s, 1H), 4.64 (s, 3H), 4.10 (s, 3H); LC-MS m/z = 418 (M + H)$^+$. |

The below compounds were prepared by procedure similar to the one described in General procedures-E, F and G with appropriate variations in reactants, quantities of reagents and reaction conditions. The physiochemical characteristics of the compounds are summarized herein below table.

| Comp No. | Structure | General Procedure | Analytical data |
|---|---|---|---|
| 3 | 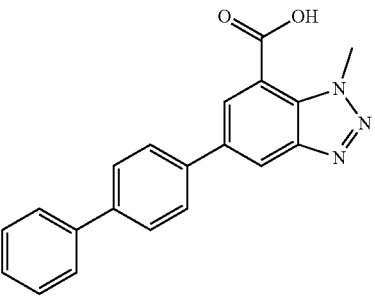 [SMILES: Cn1nnc2cc(-c3ccc(-c4ccccc4)cc3)cc(C(=O)O)c21] | F | $^1$H NMR (400 MHz, DMSO-d6): δ 13.34 (bs, 1H), 8.53 (s, 1H), 8.38 (s, 1H), 7.93-7.91 (d, J = 8.4 Hz, 2H), 7.84-7.82 (d, J = 8.8 Hz, 2H), 7.76-7.74 (d, J = 7.6 Hz, 2H), 7.53-7.40 (m, 3H), 4.58 (s, 3H) and LC-MS m/z = 330.1 (M + H)$^+$. |
| 4 | 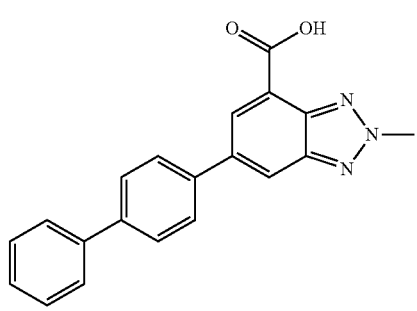 [SMILES: Cn1nc2cc(-c3ccc(-c4ccccc4)cc3)cc(C(=O)O)c2n1] | F | $^1$H NMR (400 MHz, DMSO-d6): δ 13.34 (bs, 1H), 8.51 (s, 1H), 8.28 (s, 1H), 7.97-7.95 (d, J = 8.4 Hz, 2H), 7.87-7.85 (d, J = 8.4 Hz, 2H), 7.78-7.76 (d, J = 7.6 Hz, 2H), 7.53-7.41 (m, 3H), 4.42 (s, 3H) and LC-MS m/z = 330.1 (M + H)$^+$. |

| Comp No. | Structure | General Procedure | Analytical data |
|---|---|---|---|
| 5 | 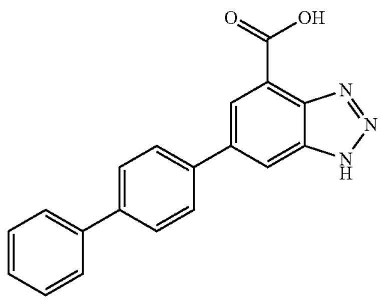 [SMILES: O=C(O)c1cc(-c2ccc(-c3ccccc3)cc2)cc2[nH]nnc12] | F | $^1$H NMR (400 MHz, DMSO-d6): δ 13.34 (bs, 1H), 8.64 (s, 1H), 8.43 (s, 1H), 7.92 (d, J = 8.4 Hz, 2H), 7.86 (d, J = 8.4 Hz, 2H), 7.76 (d, J = 7.2 Hz, 2H), 7.55-7.41 (m, 3H) and LC-MS m/z = 316.1 (M + H)$^+$. |
| 6 | 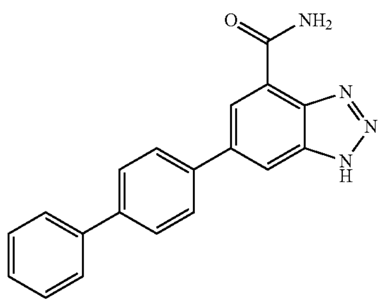 [SMILES: NC(=O)c1cc(-c2ccc(-c3ccccc3)cc2)cc2[nH]nnc12] | F and G | $^1$H NMR (400 MHz, DMSO-d6): δ 15.9 (bs, 1H), 8.61 (s, 1H), 8.48 (s, 1H), 8.41 (s, 1H), 7.98 (d, J = 8.4 Hz, 2H), 7.84 (d, J = 8.4 Hz, 2H), 7.77-7.75 (m 3H), 7.52-7.38 (m, 3H) and LC-MS m/z = 315.1 (M + H)$^+$. |
| 7 | 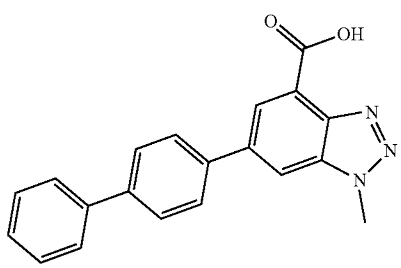 [SMILES: Cn1nnc2c(C(=O)O)cc(-c3ccc(-c4ccccc4)cc3)cc21] | F | $^1$H NMR (400 MHz, DMSO-d6): δ 13.9 (bs, 1H), 8.63 (s, 1H), 8.39 (s, 1H), 7.94-7.92 (d, J = 8.4 Hz, 2H), 7.83-7.81 (d, J = 8.4 Hz, 2H), 7.76-7.74 (d, J = 7.2 Hz, 2H), 7.52-7.40 (m, 3H), 4.52 (s, 3H) and LC-MS m/z = 330.1 (M + H)$^+$. |
| 8 | 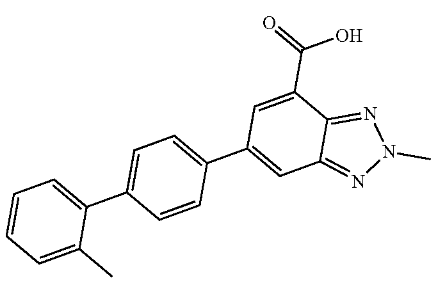 [SMILES: Cc1ccccc1-c1ccc(-c2cc(C(=O)O)c3nn(C)nc3c2)cc1] | F | $^1$H NMR (400 MHz, DMSO-d6): δ 13.39 (bs, 1H), 8.50 (s, 1H), 8.28 (s, 1H), 7.93-7.91 (d, J = 7.6 Hz, 2H), 7.54-7.52 (d, J = 8.4 Hz, 2H), 7.35-7.27 (m, 4H), 4.41 (s, 3H) 2.30 (s, 3H) and LC-MS m/z = 344.1 (M + H)$^+$. |
| 9 | 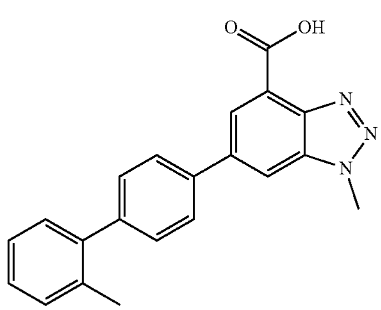 [SMILES: Cc1ccccc1-c1ccc(-c2cc(C(=O)O)c3nnn(C)c3c2)cc1] | F | $^1$H NMR (400 MHz, DMSO-d6): δ 8.64 (s, 1H), 8.40 (s, 1H), 7.90-7.88 (d, J = 8.4 Hz, 2H), 7.51-7.49 (d, J = 7.6 Hz, 2H), 7.32-7.27 (m, 4H), 4.52 (s, 3H) 2.30 (s, 3H) and LC-MS m/z = 344.2 (M + H)$^+$. |

| Comp No. | Structure | General Procedure | Analytical data |
|---|---|---|---|
| 10 | 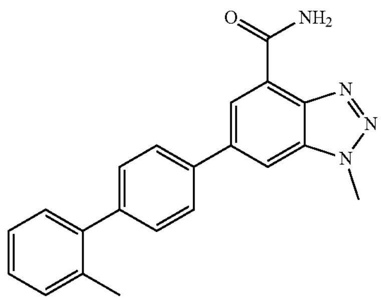 [SMILES: Cc1ccccc1-c1ccc(-c2cc(C(N)=O)c3nnn(C)c3c2)cc1] | G | $^1$H NMR (400 MHz, DMSO-d6): δ 8.54 (s, 1H), 8.49 (s, 1H), 8.34 (s, 1H), 8.14 (s, 1H), 7.93 (d, J = 8.4 Hz, 2H), 7.54 (d, J = 8.4 Hz, 2H), 7.34-7.28 (m, 4H), 4.45 (s, 3H), 2.30 (s, 3H) and LC-MS m/z = 343.2 (M + H)$^+$. |
| 11 | 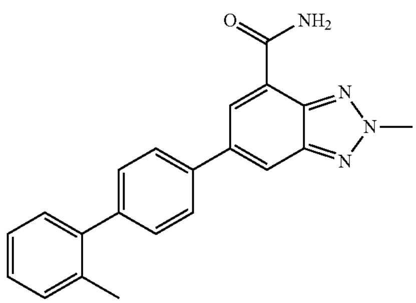 [SMILES: Cc1ccccc1-c1ccc(-c2cc(C(N)=O)c3nn(C)nc3c2)cc1] | F and G | $^1$H NMR (400 MHz, DMSO-d6): δ 8.54 (s, 1H), 8.49 (s, 1H), 8.34 (s, 1H), 8.14 (s, 1H), 7.93-7.91 (d, J = 8.4 Hz, 2H), 7.54-7.52 (d, J = 8.4 Hz, 2H), 7.34-7.28 (m, 4H), 4.45 (s, 3H), 2.30 (s, 3H) and LC-MS m/z = 343.2 (M + H)$^+$. |
| 12 | 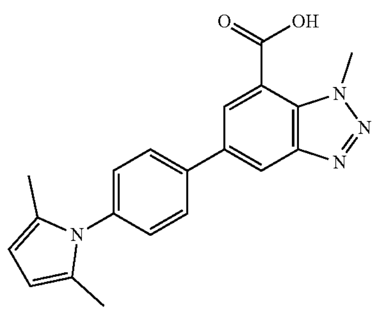 [SMILES: Cc1ccc(C)n1-c1ccc(-c2cc(C(=O)O)c3c(c2)nnn3C)cc1] | F | $^1$H NMR (400 MHz, DMSO-d6): δ 13.8 (bs, 1H), 8.67 (s, 1H), 8.40 (s, 1H), 7.97 (d, J = 8 Hz, 2H), 7.42 (d, J = 8.4 Hz, 2H), 5.83 (s, 2H), 4.52 (s, 3H), 2.03 (s, 6H) and LC-MS m/z: 347.2 (M + H)$^+$. |
| 13 | 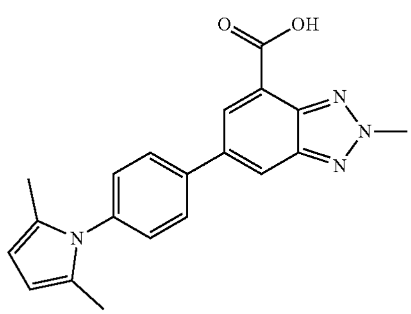 [SMILES: Cc1ccc(C)n1-c1ccc(-c2cc(C(=O)O)c3nn(C)nc3c2)cc1] | F | $^1$H NMR (400 MHz, DMSO-d6): δ 13.38 (bs, 1H), 8.56 (s, 1H), 8.37 (s, 1H), 7.96 (d, J = 8 Hz, 2H), 7.42 (d, J = 8.4 Hz, 2H), 5.83 (s, 2H), 4.58 (s, 3H), 2.03 (s, 6H) and LC-MS m/z: 347.2 (M + H)$^+$. |
| 14 | 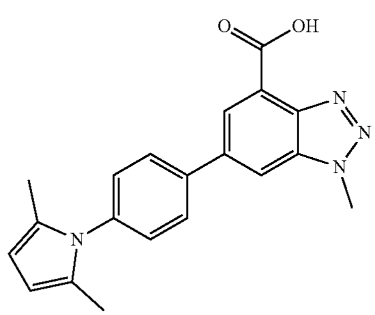 [SMILES: Cc1ccc(C)n1-c1ccc(-c2cc(C(=O)O)c3nnn(C)c3c2)cc1] | F | $^1$H NMR (400 MHz, DMSO-d6): δ 13.38 (bs, 1H), 8.53 (s, 1H), 8.27 (s, 1H), 7.98 (d, J = 8.4 Hz, 2H), 7.45 (d, J = 8.4 Hz, 2H), 5.84 (s, 2H), 4.41 (s, 3H), 2.03 (s, 6H) and LC-MS m/z: 347.2 (M + H)$^+$. |

-continued
| Comp No. | Structure | General Procedure | Analytical data |
|---|---|---|---|
| 15 | 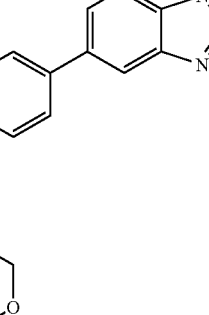 | E and F | ¹H NMR (400 MHz, DMSO-d6): δ 13.38 (bs, 1H), 8.62 (s, 1H), 8.38 (s, 1H), 7.93 (d, J = 8.4 Hz, 2H), 7.82 (d, J = 8.4 Hz, 2H), 7.67-7.63 (m, 3H), 7.48-7.44 (m, 1H), 7.35 (d, J = 8 Hz, 1H), 4.5 (s, 3H), 3.61 (m, 6H), 2.43 (m, 4H) and LC-MS m/z: 429.2 (M + H)⁺. |
| 16 | 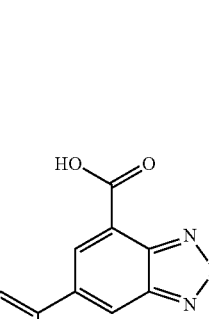 | E and F | ¹H NMR (400 MHz, DMSO-d6): δ 13.38 (bs, 1H), 8.52 (s, 1H), 8.38 (s, 1H), 7.93 (d, J = 8 Hz, 2H), 7.83 (d, J = 8.4 Hz, 2H), 7.67-7.64 (m, 2H), 7.48-7.45 (t, J = 7.6 Hz, 1H), 7.36 (d, J = 8 Hz, 1H), 4.58 (s, 3H), 3.60 (m, 6H), 2.43 (m, 4H) and LC-MS m/z: 429.2 (M + H)⁺. |
| 17 | 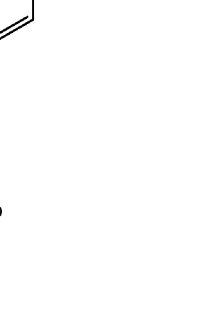 | E and F | ¹H NMR (400 MHz, DMSO-d6): δ 11.82 (bs, 1H), 8.20 (s, 1H), 8.06 (s, 1H), 7.83-7.61 (m, 6H), 7.44 (t, J = 7.6 Hz, 2H), 7.34 (d, J = 7.6 Hz, 1H), 4.54 (s, 3H), 3.74 (s, 2H), 1.74 (m, 4H), 1.23 (m, 4H) and LC-MS m/z: 413.2 (M + H)⁺. |

| Comp No. | Structure | General Procedure | Analytical data |
|---|---|---|---|
| 18 | 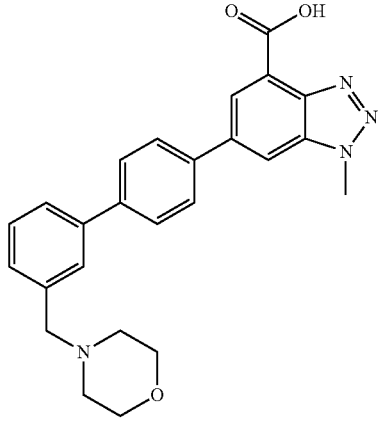 [SMILES: Cn1nnc2c(C(=O)O)cc(-c3ccc(-c4cccc(CN5CCOCC5)c4)cc3)cc21] | E and F | $^1$H NMR (400 MHz, DMSO-d6): δ 13.2 (bs, 1H), 8.49 (s, 1H), 8.27 (s, 1H), 7.96 (d, J = 8 Hz, 2H), 7.85 (d, J = 8.4 Hz, 2H), 7.67-7.64 (m, 2H), 7.48-7.46 (m, 1H), 7.44-7.34 (m, 1H), 4.44 (s, 3H), 3.60-3.57 (m, 6H), 2.41 (m, 4H) and LC-MS m/z = 429.2 (M + H)$^+$. |
| 19 | 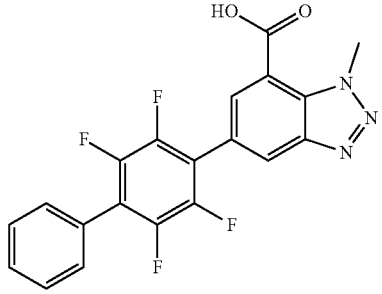 [SMILES: Cn1nnc2cc(-c3c(F)c(F)c(-c4ccccc4)c(F)c3F)cc(C(=O)O)c21] | F | $^1$H NMR (400 MHz, DMSO-d6): δ 13.8 (bs, 1H), 8.60 (s, 1H), 7.59 (s, 1H), 7.65-755. (m, 5H), 4.45 (s, 3H) and LC-MS m/z = 402.1 (M + H)$^+$. |
| 20 | 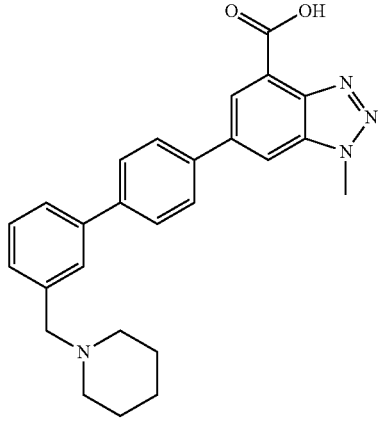 [SMILES: Cn1nnc2c(C(=O)O)cc(-c3ccc(-c4cccc(CN5CCCCC5)c4)cc3)cc21] | E and F | $^1$H NMR (400 MHz, DMSO-d6): δ 8.37 (s, 1H), 8.20 (s, 1H), 7.81 (s, 1H), 7.71-7.66 (m, 5H), 7.50-7.46 (m, 1H), 7.38-7.37 (m, 1H), 4.45 (s, 3H), 3.88 (s, 2H), 2.80-2.65 (m, 4H), 1.72-1.61 (m, 4H), 1.458 (m, 2H) and LC-MS m/z = 427.3 (M + H)$^+$. |
| 21 | 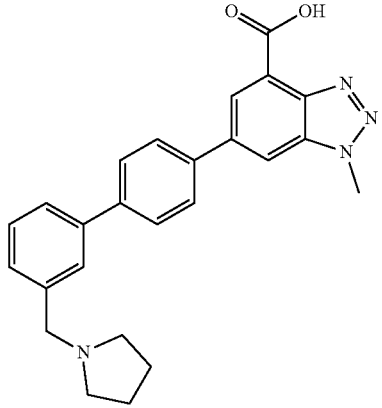 [SMILES: Cn1nnc2c(C(=O)O)cc(-c3ccc(-c4cccc(CN5CCCC5)c4)cc3)cc21] | E and F | $^1$H NMR (400 MHz, DMSO-d6): δ 12.2 (bs, 1H), 8.34 (s, 1H), 8.21 (s, 1H), 7.91-7.81 (m, 4H), 7.70-7.63 (m, 2H), 7.46-7.36 (m, 2H), 4.40 (s, 3H), 3.73 (s, 2H), 3.45-3.40 (m, 4H), 1.80-1.65 (m, 4H) and LC-MS m/z = 413.3 (M + H)$^+$. |

| Comp No. | Structure | General Procedure | Analytical data |
|---|---|---|---|
| 22 | 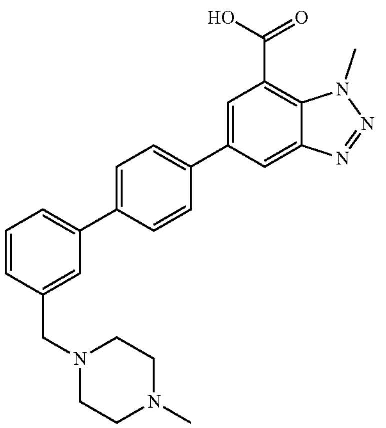 [SMILES: CN1CCN(Cc2cccc(-c3ccc(-c4cc(C(=O)O)c5c(c4)nnn5C)cc3)c2)CC1] | E and F | $^1$H NMR (400 MHz, DMSO-d6): δ 12.2 (bs, 1H), 8.58 (s, 1H), 8.35 (s, 1H), 7.92 (d, J = 8.4 Hz, 2H), 7.81 (d, J = 8.4 Hz, 2H), 7.67-7.65 (m, 2H), 7.49-7.45 (m, 1H), 7.35-7.33 (m, 1H), 4.52 (s, 3H), 3.65 (s, 2H), 2.87-2.67 (m, 4H), 2.62-2.56 (m, 4H), 2.50 (s, 3H) and LC-MS m/z = 442.3 (M + H)$^+$. |
| 23 | 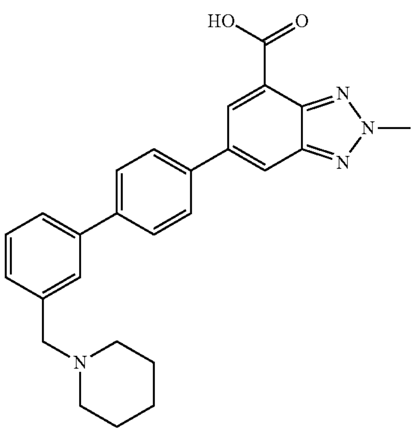 [SMILES: Cn1nc2cc(-c3ccc(-c4cccc(CN5CCCCC5)c4)cc3)cc(C(=O)O)c2n1] | E and F | $^1$H NMR (400 MHz, DMSO-d6): δ 12.36 (bs, 1H), 8.51 (m, 1H), 8.37 (s, 1H), 7.92-7.80 (m, 4H), 7.68-7.64 (m, 2H), 7.48-7.44 (m, 1H), 7.35-7.33 (m, 1H), 4.58 (s, 3H), 3.63 (s, 2H), 2.56-2.45 (m, 4H), 1.54-1.23 (m, 6H) and LC-MS m/z = 427.3 (M + H)$^+$. |
| 24 | 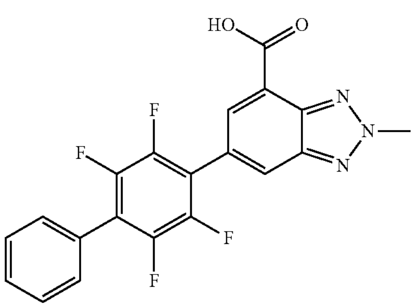 [SMILES: Cn1nc2cc(-c3c(F)c(F)c(-c4ccccc4)c(F)c3F)cc(C(=O)O)c2n1] | F | $^1$H NMR (400 MHz, DMSO-d6): δ 8.33 (s, 1H), 8.03 (s, 1H), 7.59-7.45 (m, 5H), 4.59 (s, 3H) and LC-MS m/z = 402.1 (M + H)$^+$. |
| 25 | 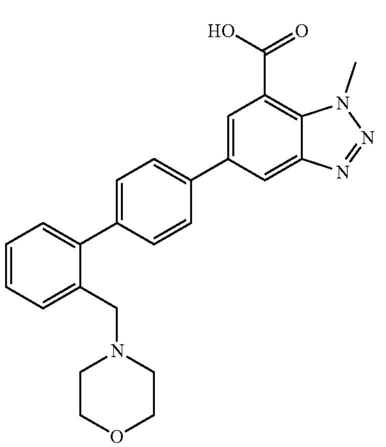 [SMILES: Cn1nnc2cc(-c3ccc(-c4ccccc4CN4CCOCC4)cc3)cc(C(=O)O)c21] | E and F | $^1$H NMR (400 MHz, DMSO-d6): δ 8.67 (s, 1H), 8.43 (s, 1H), 7.96-7.94 (m, 3H), 7.54-7.50 (m, 4H), 7.41-7.40 (m, 1H), 4.53 (s, 3H), 4.38 (bs, 2H), 3.77-3.72 (m, 4H), 3.15 (m, 2H), 2.82 (m, 2H) and LC-MS m/z = 429.3 (M + H)$^+$. |

-continued

| Comp No. | Structure | General Procedure | Analytical data |
|---|---|---|---|
| 26 | 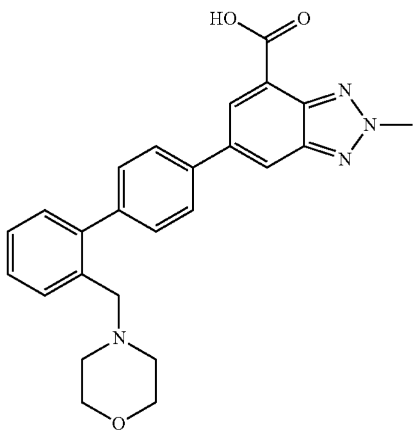 [SMILES: Cn1nc2cc(-c3ccc(-c4ccccc4CN4CCOCC4)cc3)cc(C(=O)O)c2n1] | E and F | ¹H NMR (400 MHz, DMSO-d6): δ 13.36 (s, 1H), 8.56 (s, 1H), 8.41 (s, 1H), 7.95 (d, J = 8 Hz, 2H), 7.81 (m, 1H), 7.59-7.51 (m, 4H), 7.44-7.42 (m, 1H), 4.59 (s, 3H), 4.40 (bs, 2H), 3.82-3.72 (m, 4H), 3.18 (m, 2H), 2.82 (m, 2H) and LC-MS m/z = 429.3 (M + H)⁺. |
| 27 | 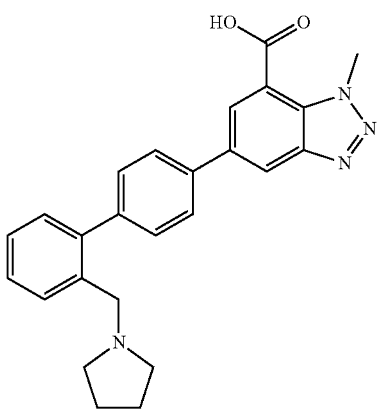 [SMILES: Cn1nnc2cc(-c3ccc(-c4ccccc4CN4CCCC4)cc3)cc(C(=O)O)c21] | E and F | ¹H NMR (400 MHz, DMSO-d6): δ 13.78 (bs, 1H), 8.67 (s, 1H), 8.42 (s, 1H), 8.04 (m, 1H), 7.97 (d, J = 8 Hz, 2H), 7.53-7.40 (m, 4H), 7.39-7.38 (m, 1H), 4.52 (s, 3H), 4.39 (s, 2H), 3.4 (m, 2H), 2.79 (m, 2H), 1.81 (m, 4H) and LC-MS m/z = 413.2 (M + H)⁺. |
| 28 | 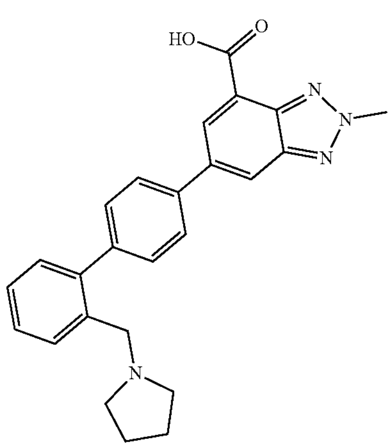 [SMILES: Cn1nc2cc(-c3ccc(-c4ccccc4CN4CCCC4)cc3)cc(C(=O)O)c2n1] | E and F | ¹H NMR (400 MHz, DMSO-d6): δ 13.36 (s, 1H), 8.56 (s, 1H), 8.40 (s, 1H), 7.96 (d, J = 8 Hz, 2H), 7.91-7.89 (m, 1H), 7.55-7.39 (m, 5H), 4.59 (s, 3H), 4.41 (s, 2H), 3.32 (m, 2H), 2.81 (m, 2H), 1.81 (m, 4H) and LC-MS m/z = 413.3 (M + H)⁺. |

-continued

| Comp No. | Structure | General Procedure | Analytical data |
|---|---|---|---|
| 29 | 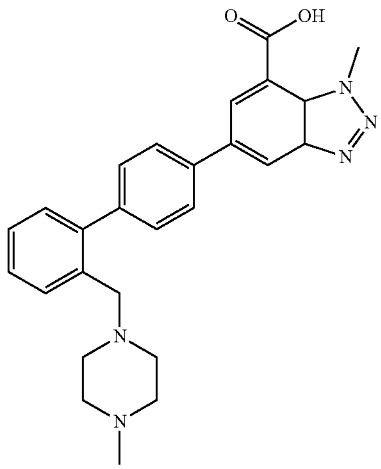 [SMILES: CN1CCN(Cc2ccccc2-c2ccc(C3=CC4N=NN(C)C4C(C(=O)O)=C3)cc2)CC1] | E and F | $^1$H NMR (400 MHz, DMSO-d6): δ 13.21 (s, 1H), 8.66 (s, 1H), 8.42 (s, 1H), 7.92 (d, J = 8 Hz, 2H), 7.55 (d, J = 8 Hz, 2H), 7.47 (m, 2H), 7.37 (m, 2H), 4.52 (s, 3H), 3.56 (s, 2H), 3.40 (m, 2H), 3.14 (m, 4H), 2.74 (s, 3H) and LC-MS m/z = 442.3 (M + H)$^+$. |
| 30 | 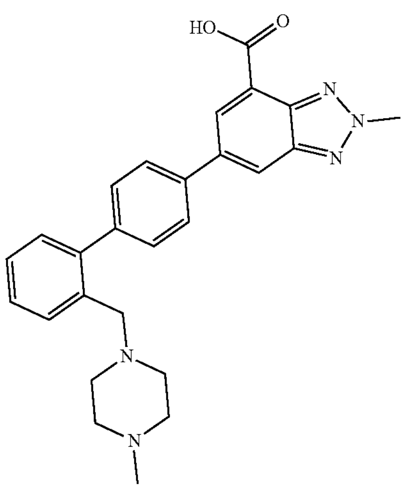 [SMILES: CN1CCN(Cc2ccccc2-c2ccc(-c3cc(C(=O)O)c4nn(C)nc4c3)cc2)CC1] | E and F | $^1$H NMR (400 MHz, DMSO-d6): δ 13.26 (s, 1H), 8.55 (s, 1H), 8.40 (s, 1H), 7.92 (d, J = 8 Hz, 2H), 7.56 (d, J = 8 Hz, 2H), 7.48 (m, 2H), 7.38 (m, 2H), 4.59 (s, 3H), 3.93 (m, 2H), 3.44 -3.42 (m, 4H), 3.16-3.14 (m, 4H), 2.77 (s, 3H) and LC-MS m/z = 442.3 (M + H)$^+$. |
| 31 | 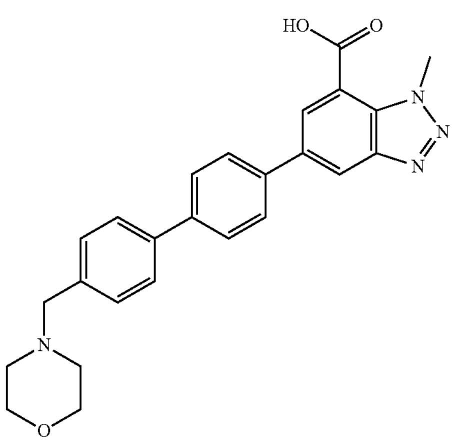 [SMILES: Cn1nnc2cc(-c3ccc(-c4ccc(CN5CCOCC5)cc4)cc3)cc(C(=O)O)c21] | E and F | $^1$H NMR (400 MHz, DMSO-d6): δ 8.63 (s, 1H), 8.39 (s, 1H), 7.92 (d, J = 8 Hz, 2H), 7.82 (d, J = 8 Hz, 2H), 7.73 (d, J = 8 Hz, 2H), 7.45 (d, J = 8 Hz, 2H), 4.52 (s, 3H), 3.61 (m, 6H), 2.74-2.61 (m, 4H) and LC-MS m/z = 429.3 (M + H)$^+$. |

| Comp No. | Structure | General Procedure | Analytical data |
|---|---|---|---|
| 32 | (structure) | F | $^1$H NMR (400 MHz, DMSO-d6): δ 13.8 (bs, 1H), 10.06 (s, 1H), 8.63 (d, J = 1.6 Hz, 1H), 8.38 (d, J = 1.6 Hz, 1H), 7.98-7.93 (m, 3H), 7.75 (d, J = 8.4 Hz, 2H), 7.61-7.58 (m, 1H), 7.42-7.40 (m, 2H), 4.52 (s, 3H), 2.05 (s, 3H) and LC-MS m/z = 387.1 (M + H)$^+$. |
| 33 | (structure) | E and F | $^1$H NMR (400 MHz, DMSO-d6): δ 13.98 (bs, 1H), 8.63 (s, 1H), 8.25 (s, 1H), 7.78-7.70 (m, 4H), 4.55 (s, 3H), 4.53 (s, 2H), 3.93-3.79 (m, 4H), 3.21 (m, 4H) and LC-MS m/z = 501.2 (M + H)$^+$. |
| 34 | (structure) | E and F | $^1$H NMR (400 MHz, DMSO-d6): δ 8.39 (s, 1H), 8.07 (s, 1H), 7.65-7.54 (m, 4H), 4.54 (s, 3H), 3.87 (s, 2H), 2.68 (m, 4H), 1.63 (m, 4H), 1.47 (m, 2H) and LC-MS m/z = 499.2 (M + H)$^+$. |

| Comp No. | Structure | General Procedure | Analytical data |
|---|---|---|---|
| 35 | (structure) | E and F | ¹H NMR (400 MHz, DMSO-d6): δ 12.4 (bs, 1H), 8.4 (s, 1H), 8.04 (s, 1H), 7.51-7.49 (m, 4H), 4.55 (s, 3H), 3.63 (s, 3H), 2.74-2.67 (m, 6H), 2.25-2.22 (m, 4H) and LC-MS m/z = 514.2 (M + H)⁺. |
| 36 | (structure) | E and F | ¹H NMR (400 MHz, DMSO-d6): δ 9.8 (s, 1H), 8.11 (s, 1H), 7.90 (s, 1H), 7.85 (s, 1H), 7.64-7.53 (m, 3H), 4.53 (s, 3H), 4.24 (s, 2H), 3.36-3.16 (m, 1H), 1.34 (d, J = 6.4 Hz, 6H) and LC-MS m/z = 473.2 (M + H)⁺. |
| 37 | (structure) | E and F | ¹H NMR (400 MHz, DMSO-d6): δ 13.98 (bs, 1H), 8.95 (s, 1H), 8.63 (s, 1H), 8.25 (s, 1H), 7.71-7.65 (m, 4H), 4.55 (s, 3H), 4.26 (s, 2H), 2.63 (s, 3H) and LC-MS m/z = 445.1 (M + H)⁺. |

| Comp No. | Structure | General Procedure | Analytical data |
|---|---|---|---|
| 38 | 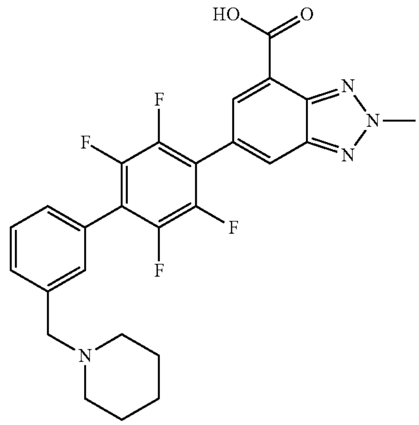 [SMILES: Cn1nc2cc(-c3c(F)c(F)c(-c4cccc(CN5CCCCC5)c4)c(F)c3F)cc(C(=O)O)c2n1] | E and F | ¹H NMR (400 MHz, DMSO-d6): δ 13.46 (bs, 1H), 8.53 (s, 1H), 8.19 (s, 1H), 7.82-7.69 (m, 4H), 4.62 (s, 3H), 4.37 (s, 2H), 2.88-2.66 (m, 2H), 1.79-1.68 (m, 5 H) 1.38-1.23 (m, 2H) and LC-MS m/z = 499.2 (M + H)⁺. |
| 39 | 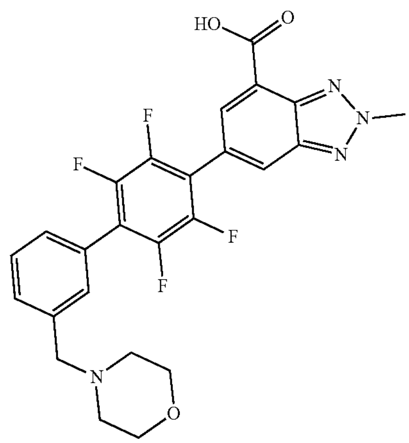 [SMILES: Cn1nc2cc(-c3c(F)c(F)c(-c4cccc(CN5CCOCC5)c4)c(F)c3F)cc(C(=O)O)c2n1] | E and F | ¹H NMR (400 MHz, DMSO-d6): δ 13.48 (bs, 1H), 8.54 (s, 1H), 8.19 (s, 1H), 7.81-7.72 (m, 4H), 4.62 (s, 3H), 4.46 (s, 2H), 3.98 (m, 2H), 3.78-3.72 (m, 2H), 3.15 (m, 4H) and LC-MS m/z = 501.2 (M + H)⁺. |
| 40 | 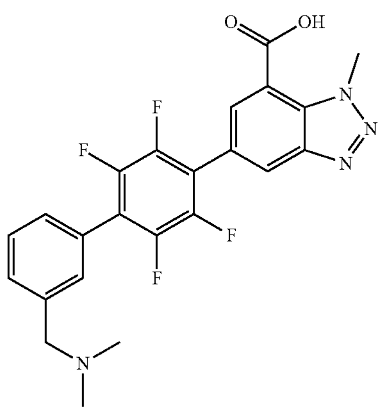 [SMILES: CN(C)Cc1cccc(-c2c(F)c(F)c(-c3cc(C(=O)O)c4c(c3)nnn4C)c(F)c2F)c1] | E and F | ¹H NMR (400 MHz, DMSO-d6): δ 13.8 (bs, 1H), 8.62 (s, 1H), 8.25 (s, 1H), 7.78-7.70 (m, 4H), 4.55 (s, 3H), 4.38 (s, 2H), 2.75 (s, 6H) and LC-MS m/z = 459.2 (M + H)⁺. |

Pharmacological Activity

Measurement of DHODH Inhibitory Enzyme Activity (In Vitro Assays)

The DHODH activity assay is a coupled enzyme assay in which oxidation of DHO and subsequent reduction of ubiquinone are stoichiometrically equivalent to the reduction of DCIP (2,6-dichlorophenol). The reduction of DCIP is accompanied by a loss of absorbance at 610 nm.

Preparation of solutions/reagents:

Buffer Preparation: 50 mM tris HCl, 150 mM KCl, and pH 8.0, 0.8% triton.

L-Dihydroorotic acid stock solution of 20 mM in buffer.

2, 6-Dichloroindophenol Sodium salt hydrate stock solution of 20 mM in buffer.

Decylubiquinone stock solution of 20 mM in buffer.

DMSO used as vehicle.

Procedure

5 μL of Dimethyl sulfoxide or a compound of formula (I) in DMSO solution was added to the wells of a 96 well plate. Compounds of formula (I) were measured at 10 μM.

Protein along with buffer was added, so that the total volume including the DMSO was 87 μL. Compound and protein were incubated for half an hour at room temperature after mixing. 5 µL of 20 mM solution of L-Dihydroorotic acid, 5 µL of 2 mM solution of Decylubiquinone and 3 µL of 2 mM solution of 2, 6-Dichloroindophenol sodium salt hydrate were added to the above solution (total assay volume 100 µL). The mixture was stirred for 2 min and absorbance was recorded at every 10 min at 610 nanometers.

Percent inhibition is calculated as follows:

$$100 * \frac{(Abs_{610} \text{ for reaction containing compound}) - (Abs_{610} \text{ for positive control})}{(Abs_{610} \text{ for no enzyme reaction}) - (Abs_{610} \text{ for positive control})}$$

Reaction containing compound has compound, buffer, enzyme and substrates

Positive control contains DMSO, buffer, enzyme and substrates

No Enzyme reaction contains DMSO, buffer and substrates $IC_{50}$ Determination

A 2 mM DMSO stock solution of the selected trisubstituted benzoimidazole and benzotriazole derivatives of formula (I) of the present invention to be examined was prepared. Subsequent ⅓rd dilutions were made.

5 µL of each stock of compound of formula (I) was used for each 100 µL assay. Therefore, 5 µL of the 2 mM stock provided 100 µL of 100 µM solution of compound of formula (I), when made up with buffer, protein and substrate. See also: Ulrich et al. (2001) *Eur. J. Biochem.*268, 1861-1868.

$IC_{50}$ values of the selected compounds of present invention were provided in below table, Compounds exhibiting $IC_{50}$ values<0.1 µM were grouped as 'a', compounds exhibiting $IC_{50}$ value in the range 0.101 µM to 1.0 µM were grouped as 'b' and the compounds exhibiting $IC_{50}$ value>1.0 µM were grouped as 'c'.

TABLE

DHODH inhibition activity of the selected compounds.

| Group | Compound Nos. |
|---|---|
| a | 1, 2, 8, 12, 19, 24. |
| b | 3, 4, 11, 13, 25, 29, 33, 34, 36, 38, 39, 40. |
| c | 15, 16, 17, 20, 26, 27, 30, 31, 32, 35, 37. |

Cell Based Activity
Ramos Proliferation Assay (In Vitro Assays)

Cell proliferation assay is a sensitive method for quantification of viable cells in cytotoxicity or proliferation assay. The XTT (2,3-bis[2-Methoxy-4-nitro-5-sulfophenyl]-2 H-tetrazolium-5-carboxyanilide inner salt) system is a means of measuring the activity of living cells via mitochondrial dehydrogenases. Mitochondrial dehydrogenases of viable cells cleave the tetrazolium ring of XTT, yielding orange formazon crystals which are soluble in aqueous solutions. The XTT solution is potentiated by the addition of an electron coupling agent, phenazine methosulphate (PMS) to the reaction. The resulting orange colour is spectrophotometrically measured at 450 nm. An increase or decrease in cell numbers results in a concomitant change in the amount of formazon formed, indicating the degree of cytotoxicity caused by the test material.

Preparation of Solutions/Reagents
Media Preparation

Dissolve 17.7 g IMDM (Iscove's Modified Dulbecco's Medium) powder, 1.5 g sodium bicarbonate pH 7.2-7.4 in 1 L MiliQ water, add 1% Pencilin/ Streptomycin and 10% FBS.

Dissolve 10.6 g Ham's F12 powder, 1.5 g sodium bicarbonate pH 7.2-7.4 in 1 L MiliQ water, add 1% Penicillin/ Streptomycin. DMSO used as vehicle.

1× PBS (Phosphate Buffered Saline): Dissolve 5 tablets of PBS (Sigma: Cat#P4417) in 1 L MiliQ water.
Procedure ($IC_{50}$ Determination)

Ramos cells were re-suspended to a density of 1×10⁵ cells/ ml in complete IMDM medium. 95 µL of this cell suspension was added to the 96-well plate to seed ~10,000 cells per well. The plates were incubated at 37° C. under a humidified atmosphere of 5% $CO_2$ for ~1 hour before compound addition.

Test compounds (Refer to Table 1) were dissolved in 100% DMSO to generate a 2/6/10/20 mM stock solution. A 200× concentration of the required final concentrations was prepared in DMSO. 10 µL of each concentration (200×) was then diluted in 90 µL of serum-free Ham's F12 medium to get an intermediate concentration of 20× in medium. The DMSO concentration in this step is 10% (Intermediate dilution). 5 µL of each intermediate dilution was then added in triplicates in the previously seeded 96-well plate. The final DMSO concentration was 0.5% in the experimental wells. Cells treated with 0.5% DMSO served as positive control. 100 µL, of complete IMDM medium served as media blank for data analysis. 200 µL, of 1× PBS was added in all corner wells of the assay plate. Plates were then incubated for 72 hrs in an incubator with 5% $CO_2$ at 37° C.

On termination day, 100 µl of XTT solution (1 mg/ml XTT supplemented with 25 µM PMS in Ham's F12 medium) was added to each well. Plates were incubated for 2 hrs. The amount of formazon produced was determined by reading the absorbance of the plate using VICTOR X5 multilabel plate reader at wavelength of 450 nm. The $IC_{50}$ values were determined as concentrations that reduced cell viability by 50% and the curve was plotted with GraphPad Prism 6.0.

Percent inhibition is calculated as follows:

Percent (%) Inhibition was calculated by normalizing DMSO control values to 100% using the formula:

$$\% \text{ Inhibition} = 100\% / (Abs450_{test\ compound-blank}) / (Abs450_{positive\ control-blank}) * 100$$

Test compound contains cells, test compound, IMDM medium and 0.5% DMSO

Positive control contains cells, IMDM medium and 0.5% DMSO

Blank contains IMDM medium

| Comp. No. | Maximum % Inhibition at 30 µM | $IC_{50}$ (µM) |
|---|---|---|
| 1 | 107 | 0.049 |
| 2 | 95 | 1.086 |
| 3 | 113 | 0.524 |
| 4 | 107 | 1.453 |
| 8 | 103 | 0.154 |
| 11 | 67 (at 10 µM) | ND |
| 12 | 103 | 0.362 |
| 13 | 100 | 3.882 |
| 15 | 96 | 8.406 |
| 16 | 124 | 6.141 |
| 17 | 50 | ND |

-continued

| Comp. No. | Maximum % Inhibition at 30 μM | IC$_{50}$ (μM) |
|---|---|---|
| 19 | 106 | 0.07 |
| 20 | 129 | 3.717 |
| 24 | 104 | 0.4 |
| 25 | 120 | 2.819 |
| 26 | 133 | 4.255 |
| 27 | 89 | 3.05 |
| 29 | 81 | 8.968 |
| 30 | 56 | ND |
| 31 | 81 (at 10 μM) | 1.349 |
| 32 | 74 | 14.58 |
| 34 | 111 (at 10 μM) | 0.675 |
| 38 | 92 | 1.601 |
| 39 | 96 | 1.869 |
| 40 | 84 | 11.85 |

In vitro growth inhibition of multiple human cancer cell lines by Compound 1

A tumor cell line panel screen aimed at identifying tumor cell subsets that were particularly sensitive to inhibition of DHODH with Compound 1 was performed. Compound 1 is represented by the following structural formula:

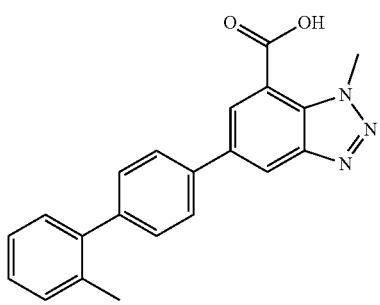 [SMILES: Cc1ccccc1-c1ccc(-c2cc(C(=O)O)c3c(c2)nnn3C)cc1]

These cell lines were treated with Compound 1 for a total of 72 hrs.

Assessment of tumor growth rates after the 72-hour treatment, as shown in FIG. 1 and Table 1, revealed that a distinct subset of cell lines (depicted by grey dots in FIG. 1) were sensitive to Compound 1. The majority of the cell lines exhibiting high sensitivity to Compound 1 are of hematopoietic origin though some solid tumors also exhibited high sensitivity (Table 1). For purposes of generating FIG. 1, sensitive cell lines were defined as exhibiting ≥75% maximal growth inhibition and a GI$_{50}$ value of <1.5 μM. Table 1 is a list of some of the sensitive cell lines to Compound 1 along with GI$_{50}$ values and max growth response. A maximum inhibition of 100 represents complete growth inhibition; a max inhibition value>100 represents cell killing.

Figure 2:
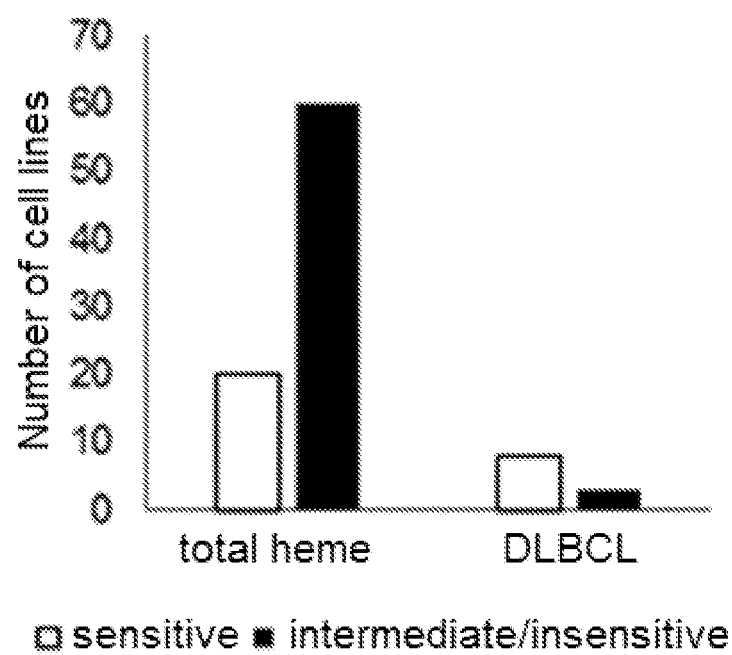
FIG. 2 shows the sensitivity of an additional panel of human cancer lines of heme lineage towards growth inhibition by Compound 1 of the invention.

A follow-up screen was performed on an expanded panel of cell lines of heme lineage in a 4-day growth assay. Growth was assessed by Cell-Titer Glo measurements on day 0 and day 4. As shown in FIG. 2, 25% of the heme lines screened (20/80) exhibited sensitivity to Compound 1, of which diffuse large B cell lymphoma (DLBCL) lines were particularly sensitive (8/11 or 73%). A subset of the heme lines that were of intermediate sensitivity (defined as >50% and <75% growth rate inhibition) or insensitive (defined as <50% growth rate inhibition) to compound 1 in this follow-up screen were subjected to extended growth assays to evaluate if increased treatment time modulated their sensitivity profile. Specifically, these heme lines were pretreated with Compound 1 for three days at the indicated concentrations and then re-plated for a standard 4-day growth assay in fresh media/drug. The vast majority of re-tested heme lines exhibited strong sensitivity to compound 1 following 7 days of treatment with Compound 1 (Table 2).

TABLE 1

GI$_{50}$ and maximum growth inhibition of various cell lines treated with Compound 1

| Cell line | Primary site | Disease | GI$_{50}$ (μM) | Maximum growth inhibition |
|---|---|---|---|---|
| OCILY8 | Hematopoietic and lymphoid tissue | Diffuse large B cell lymphoma | 0.02 | 148.2 |
| SUDHL5 | Hematopoietic and lymphoid tissue | Diffuse large B cell lymphoma | 0.02 | 117.2 |
| JVM13 | Hematopoietic and lymphoid tissue | B-prolymphocytic leukemia | 0.02 | 112.0 |
| MINO | Hematopoietic and lymphoid tissue | Mantle cell lymphoma | 0.03 | 144.9 |
| SUDHL1 | Hematopoietic and lymphoid tissue | Anaplastic large cell lymphoma | 0.04 | 186.5 |
| SR786 | Hematopoietic and lymphoid tissue | Anaplastic large cell lymphoma | 0.05 | 96.3 |
| MOLM13 | Hematopoietic and lymphoid tissue | Acute myeloid leukemia | 0.06 | 133.8 |
| RL | Hematopoietic and lymphoid tissue | Non-Hodgkin's lymphoma | 0.08 | 87.0 |
| DU4475 | Breast | Triple negative breast cancer | 0.10 | 137.4 |
| JYSE150 | Esophagus | Cancer of the esophagus (esophageal squamous cell carcinoma) | 0.10 | 78.4 |
| KYSE510 | Esophagus | Cancer of the esophagus (esophageal squamous cell carcinoma) | 0.13 | 97.5 |
| SUM159PT | Breast | Triple negative breast cancer | 0.14 | 91.2 |
| MV411 | Hematopoietic and lymphoid tissue | Child acute myeloid leukemia | 0.27 | 835 |
| DU145 | Prostate | Prostate cancer | 0.48 | 84.9 |
| CJM | Skin | Melanoma | 0.62 | 77.4 |

TABLE 2

4-day and 7-day sensitivity of various heme cell lines treated with Compound 1

| Cell line | Disease | Sensitivity 4-day | 7-day |
|---|---|---|---|
| REC-1 | Mantle cell lymphoma | * | *** |
| SUDHL4 | Diffuse large B cell lymphoma | ** | *** |
| U266B1 | Multiple myeloma | * | *** |
| LP1 | Multiple myeloma | * | *** |
| MOLP-2 | Multiple myeloma | ** | *** |
| KG-1 | Acute myeloid leukemia | * | *** |
| KMS12BM | Multiple myeloma | ** | *** |
| BDCM | Acute myeloid leukemia | ** | *** |
| HuNS1 | Multiple myeloma | * | *** |
| GDM-1 | Acute myeloid leukemia | * | ** |
| SKNO-1 | Acute myeloid leukemia | * | ** |
| Kasumi-3 | Acute myeloid leukemia | * | * |

TABLE 2-continued 4-day and 7-day sensitivity of various heme cell lines treated with Compound 1

| Cell line | Disease | Sensitivity | |
|---|---|---|---|
| | | 4-day | 7-day |
| Kasumi-6 | Acute myeloid leukemia | * | * |
| F36P | Acute myeloid leukemia | ** | *** |
| THP-1 | Acute myeloid leukemia | ** | *** |
| AML-193 | Acute myeloid leukemia | ** | *** |
| TF1 | Acute myeloid leukemia | * | *** |
| HEL | Acute myeloid leukemia | ** | *** |

\* - insensitive
\*\* - intermediate
\*\*\* - sensitive

Cancer Cell Growth Inhibition by Compound 1 is Attributed to Inhibition of DHODH DHODH catalyzes the fourth step in de novo pyrimidine biosynthesis, oxidizing dihydrorotate to orotate in the inner mitochondrial membrane. The orotate then combines with phosphoribosyl pyrophosphate (PRPP) to form orotidine-5'-monophosphate (OMP). Uridine monophosphate (UMP) is ultimately produced from OMP in the cytosol where it is utilized to make pyrimidines for RNA/DNA biosynthesis as well as for other important biosynthetic functions such as protein/lipid glycosylation and phospholipid production for membrane biosynthesis.

Figure 3:
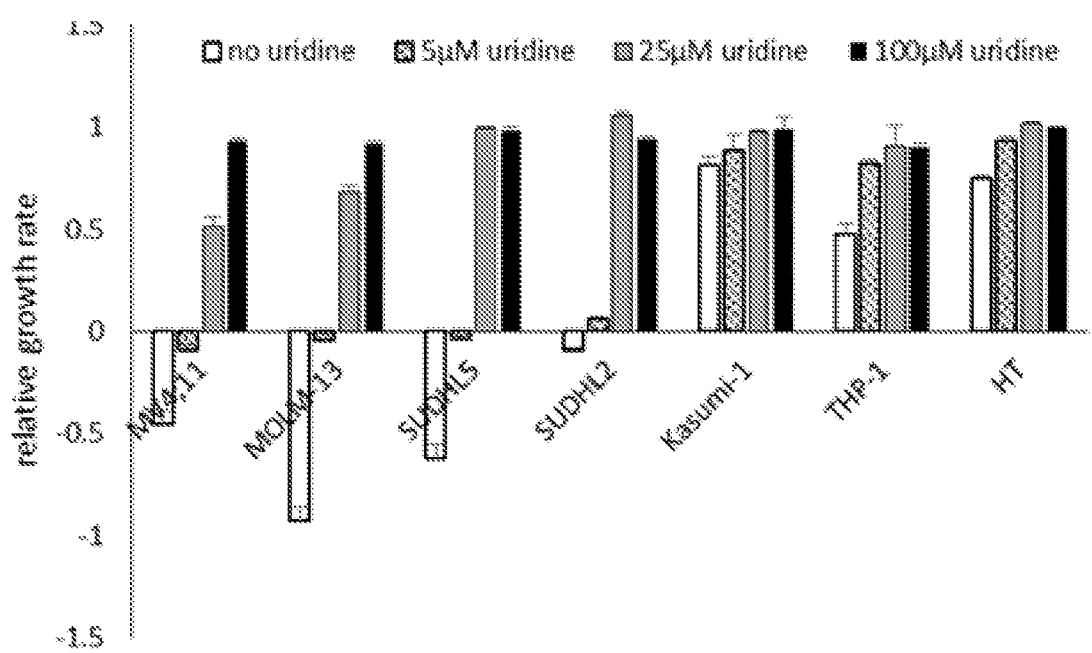
FIG. 3 shows the ability of physiologic (5 μM) and supraphysiologic (25 μM, 100 μM) concentrations of exogenous uridine to rescue the cytotoxic effects of 10 μM of compound on the indicated cancer lines.

To confirm that the effects of Compound 1 in impairing cell growth/viability were due to specific inhibition of DHODH, cell growth assays were performed with varying amounts of uridine supplemented into the medium. Supplementing medium with uridine concentrations close to physiologic (5 µM) partially rescued the effects of Compound 1 while supraphysiologic concentrations (25 µM and 100 µM) completely rescued the effects on growth of up to 10 µM of Compound 1. These results indicate that the effects of Compound 1 on growth are on-target (FIG. 3).

Figure 4A:
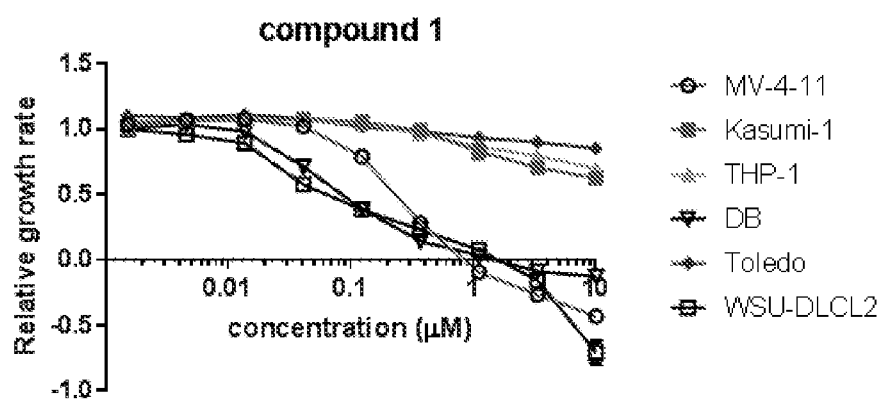
FIG. 4A shows the relative growth rate vs. concentration sensitivity profiles of MV411, Kasumi-1, THP-1, DB, Toledo and WSU-DLCL2 cell lines towards varying concentrations of Compound 1.
Figure 4B:
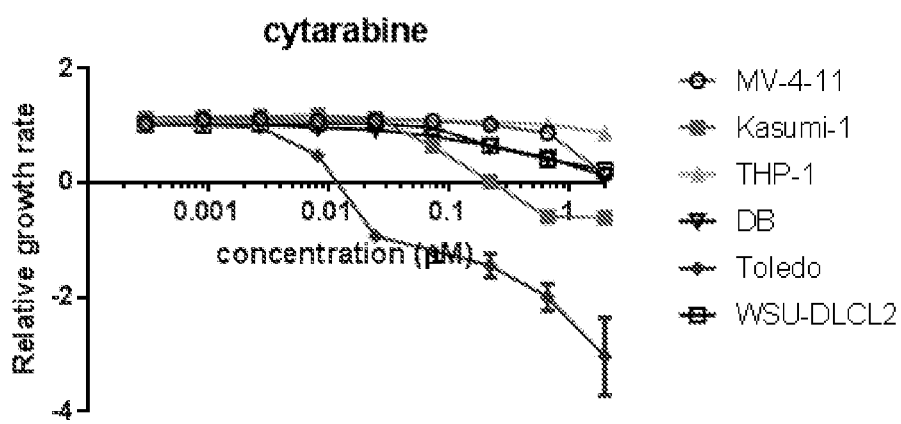
FIG. 4B shows the relative growth rate vs. concentration sensitivity profiles of MV411, Kasumi-1, THP-1, DB, Toledo and WSU-DLCL2 cell lines towards varying concentrations of cytarabine.
Figure 4C:
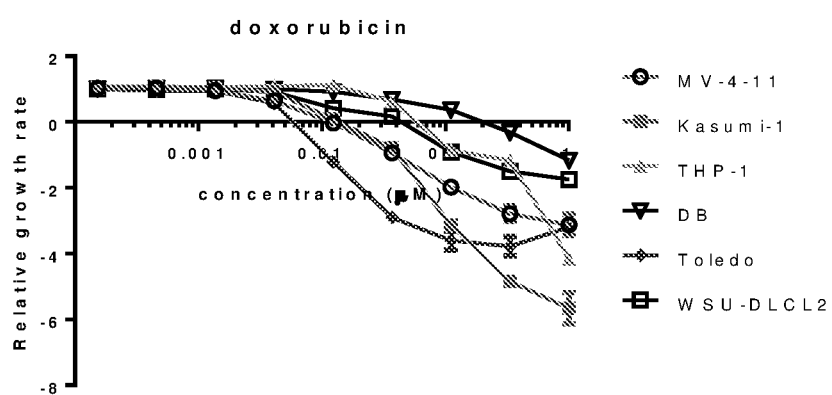
FIG. 4C shows the relative growth rate vs. concentration sensitivity profiles of MV411, Kasumi-1, THP-1, DB, Toledo and WSU-DLCL2 cell lines towards varying concentrations of doxorubicin.

Comparison of Compound 1 Sensitivity Profile Against Cytarabine and Doxorubicin Sensitivity Profiles The sensitivity profile of Compound 1 against a subset of heme lines was compared to the sensitivity profiles other agents that are used as standard of care (SOC) in heme malignancies. Consistent with its differing mechanism of action, Compound 1 displayed a sensitivity profile (FIG. 4A) distinct from cytarabine (FIG. 4B) and doxorubicin (FIG. 4C) sensitivity profiles.

Compound 1 Effectively Inhibits DHODH In Vivo and Blocks Tumor Growth in AML Xenograft Model In vivo efficacy studies with Compound 1 were performed to assess the in vitro to in vivo translation of effects on blockade of DHODH and tumor cell growth inhibition. $1 \times 10^6$ MOLM-13 cells were implanted subcutaneously into CB17 SCID mice. Mice (n=15/group) were treated with vehicle or Compound 1 at 100 mg/kg BID PO once tumors reached an average of ~150 mm³. At end of the study, tissues were collected at the indicated timepoints post-last dose for pharmacokinetic (PK) and pathway biomarker analyses.

Figure 5A:
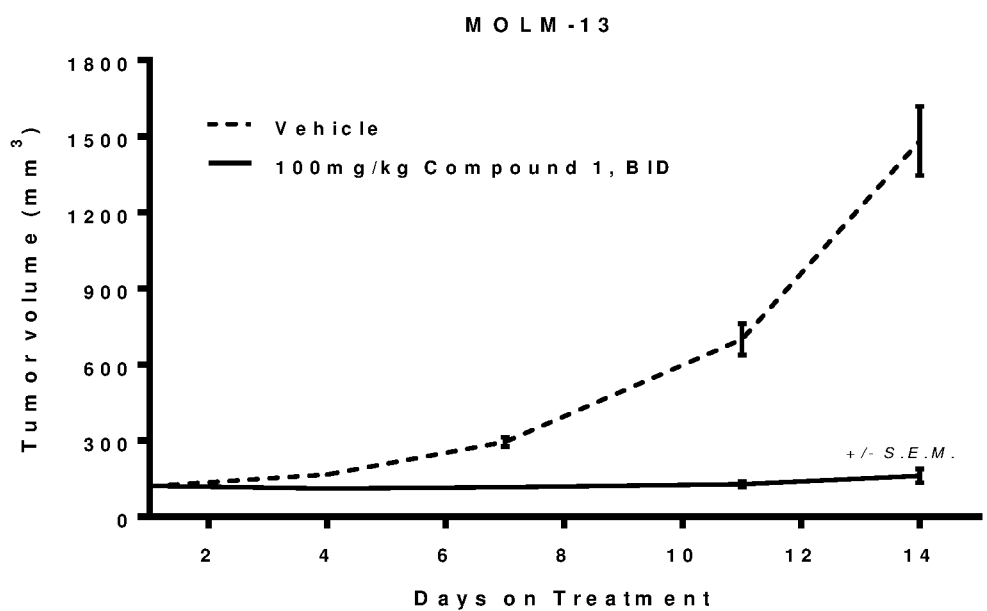
FIG. 5A shows MOLM-13 tumor growth curves in CB17 SCID mice when left untreated (vehicle) or treated with 100 mg/kg of Compound 1, BID, measured over the course of 14 days.
Figure 5B:
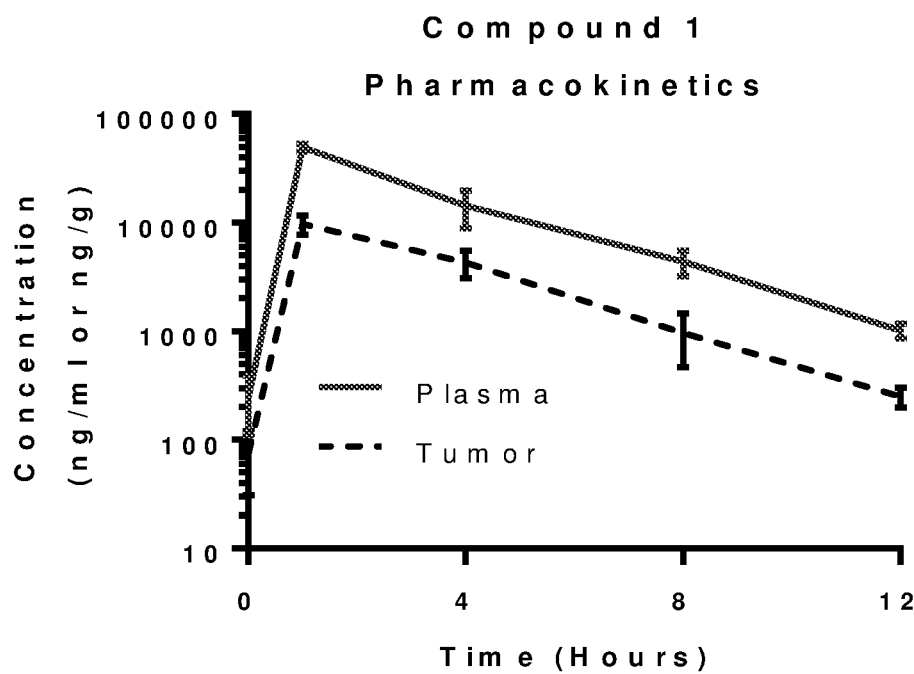
FIG. 5B shows the pharmacokinetic profiles of Compound 1 (dosage=100 mg/kg, BID) in the plasma of the CB17 SCID mice and in the implanted MOLM-13 tumors at the indicated timepoints following the last dose at end of study.
Figure 5C:
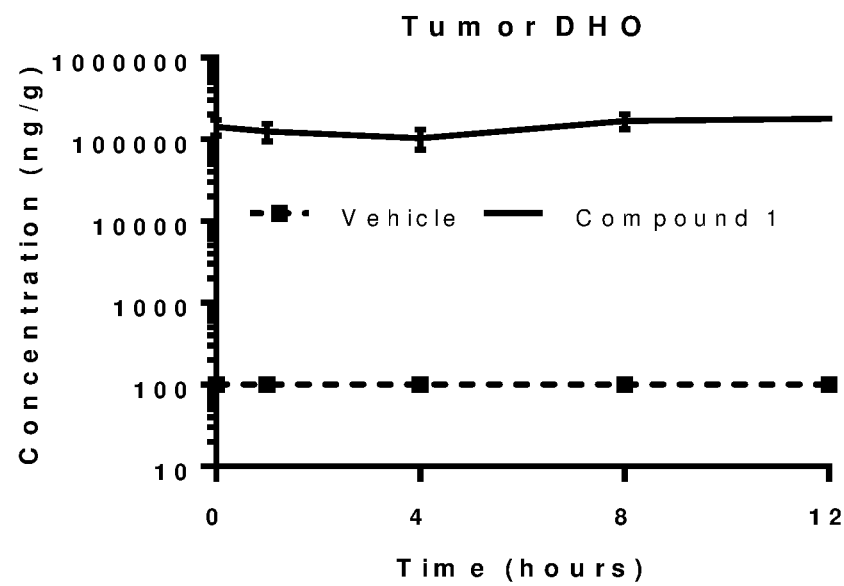
FIG. 5C shows the DHO levels in the untreated (vehicle) MOLM-13 tumors and tumors treated with Compound 1, measured over the course of 12 hrs following the last dose at end of study.
Figure 5D:
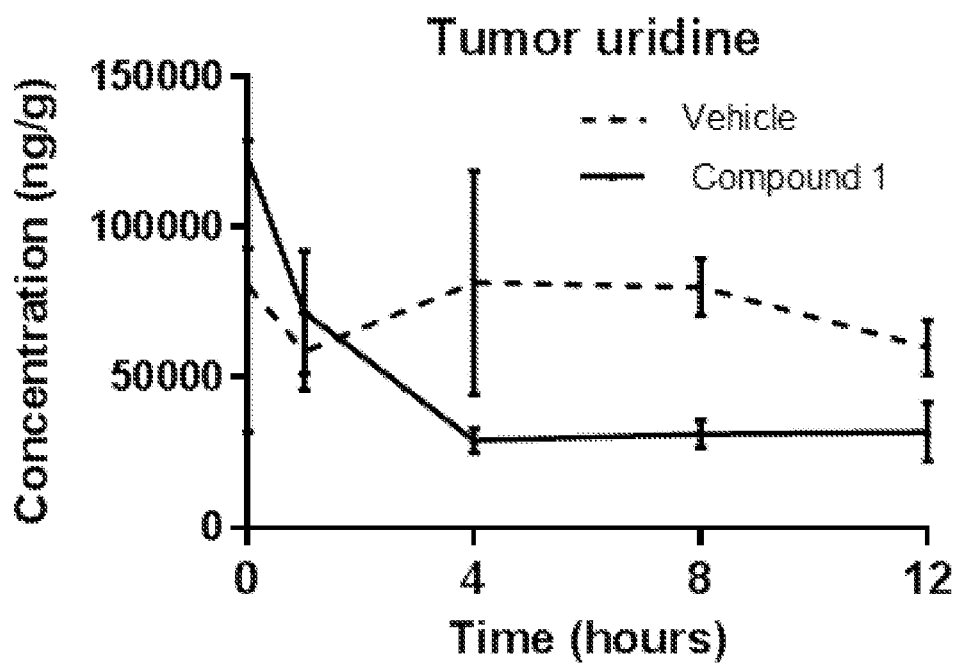
FIG. 5D shows the uridine levels in the untreated (vehicle) MOLM-13 tumors and tumors treated with Compound 1, measured over the course of 12 hrs following the last dose at end of study.
Figure 6A:
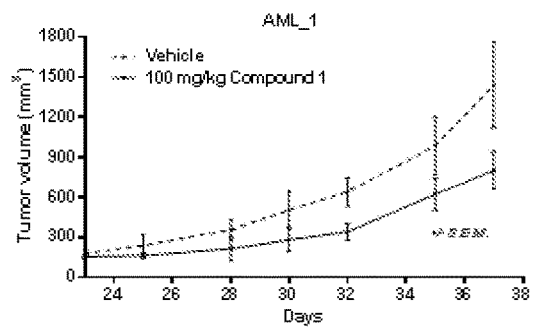
FIG. 6A shows patient-derived AML_1 tumor growth curves in CB17 SCID mice when left untreated (vehicle) or treated with 100 mg/kg of Compound 1, BID.
Figure 6B:
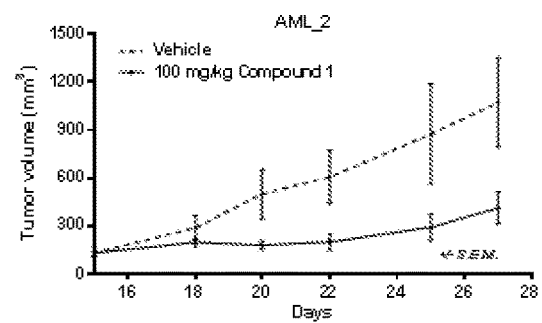
FIG. 6B shows patient-derived AML_2 tumor growth curves in CB17 SCID mice when left untreated (vehicle) or treated with 100 mg/kg of Compound 1, BID.
Figure 6C:
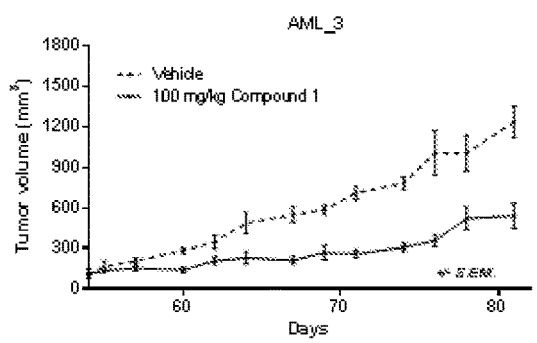
FIG. 6C shows patient-derived AML_3 tumor growth curves in CB17 SCID mice when left untreated (vehicle) or treated with 100 mg/kg of Compound 1, BID.
Figure 6D:
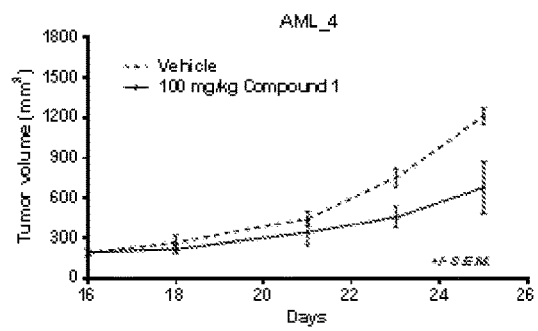
FIG. 6D shows patient-derived AML_4 tumor growth curves in CB17 SCID mice when left untreated (vehicle) or treated with 100 mg/kg of Compound 1, BID.
Figure 6E:
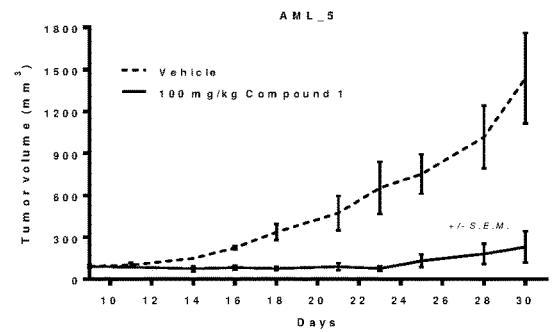
FIG. 6E shows patient-derived AML_5 tumor growth curves in CB17 SCID mice when left untreated (vehicle) or treated with 100 mg/kg of Compound 1, BID.
Figure 7A:
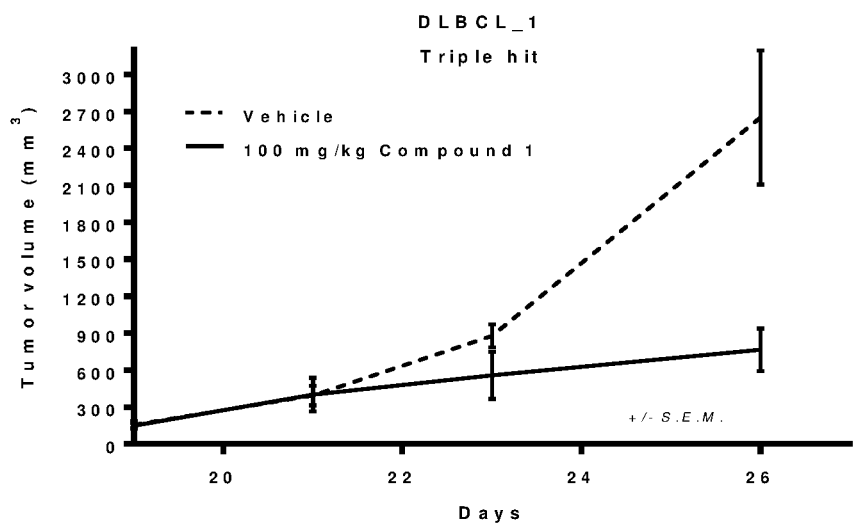
FIG. 7A shows patient-derived DLBCL 1 (triple hit model) tumor growth curves in CB17 SCID mice when left untreated (vehicle) or treated with 100 mg/kg of Compound 1, BID.
Figure 7B:
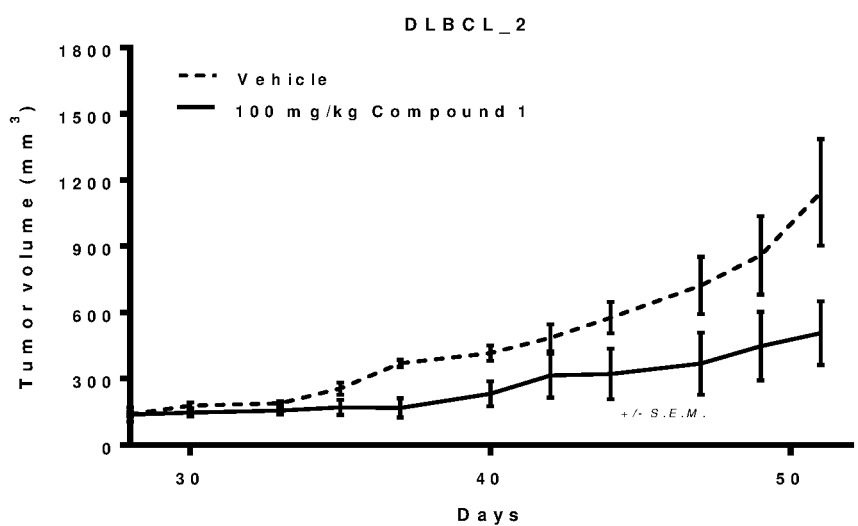
FIG. 7B shows patient-derived DLBCL_2 tumor growth curves in CB17 SCID mice when left untreated (vehicle) or treated with 100 mg/kg of Compound 1, BID.

Compound 1 administered at 100 mg/kg BID was well tolerated and resulted in near complete tumor growth inhibition (TGI) of the MOLM-13 acute myeloid leukemia (AML) xenograft model (FIG. 5A). The pharmacokinetics profile measured in the plasma and tumor shows a drop in drug concentrations by 12 hrs, supporting the BID dosing regimen (FIG. 5B). Clear evidence of target engagement was observed by the dramatic increase in tumor levels of dihydroorotate (DHO), the DHODH substrate (FIG. 5C). Baseline DHO levels were below the quantifiable limit (BQL<120 ng/g). Tumor uridine pools were concomitantly reduced by ~60% depending on the timepoint assessed (FIG. 5D).

Compound 1 Effectively Inhibits DHODH In Vivo and Blocks Tumor Growth in Patient-Derived AML and DLBCL Xenograft Models A screen was next performed using a small number of mice/group to assess efficacy of Compound 1 in AML and DLBCL patient-derived xenograft models. Tumor-bearing mice (n=3/group) were treated with vehicle or Compound 1 at 100 mg/kg BID PO.

As shown in FIGS. 6A-6E and 7A-7B, anti-tumor activity of Compound 1 was observed in all models tested, with >60% TGI in two out of five AML models (i.e., AML_2 and AML 5) and one out of two DLBCL models (DLBCL_1). The DLBCL_1 model is characterized as a triple-hit DLBCL model.

In Vitro Growth Inhibition of Double Hit Diffuse Large B Cell Lymphoma Human Cancer Cell Lines by Compound 1

Figure 8:
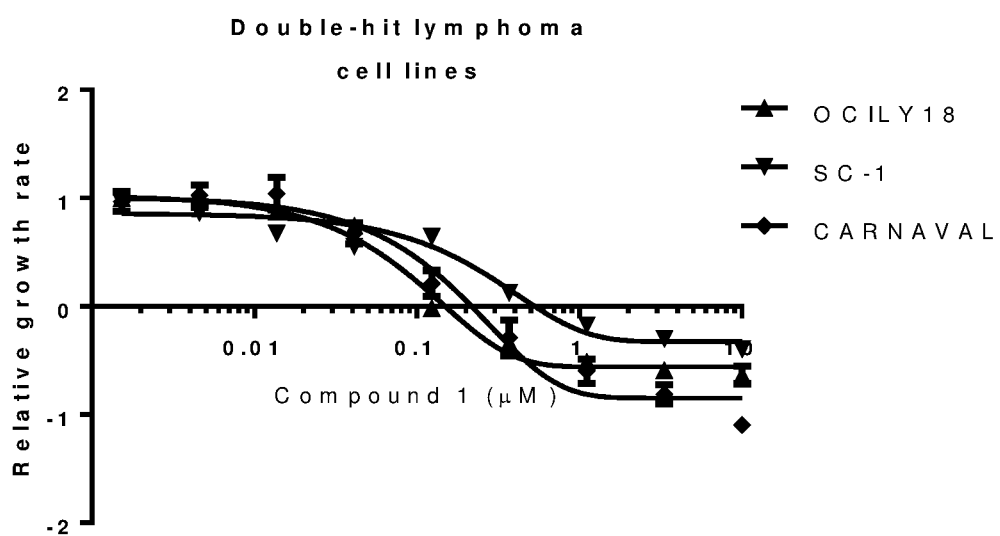
FIG. 8 is a curve showing the relative growth rate of OCILY18, SC-1 and CARNAVAL double hit diffuse large B cell lymphoma (DLBCL) cell lines treated with various concentrations of Compound 1 for 96 hours.

Three patient-derived DBLCL lymphoma cell lines classified as double-hit DLBCL, namely OCILY18, SC-1 and CARNAVAL, were found to be highly sensitive to inhibition by Compound 1 in a 96-hr growh assay (FIG. 8).

Compound 1 Effectively Blocks Tumor Growth in Patient-Derived DLBCL Xenograft Model A strong block in in vivo tumor growth was observed with Compound 1 in the OCILY-19 diffuse large B-cell lymphoma (DLBCL) xenograft model. $7 \times 10^6$ OCILY-19 cells were implanted subcutaneously into CB17 SCID mice. Mice (n=15-18/group) were treated with vehicle or Compound 1 at the indicated dose/frequency once tumors reached an average of ~150 mm³. Tissues were collected at the indicated timepoints post-last dose for PK and biomarker analyses.

Figure 9A:
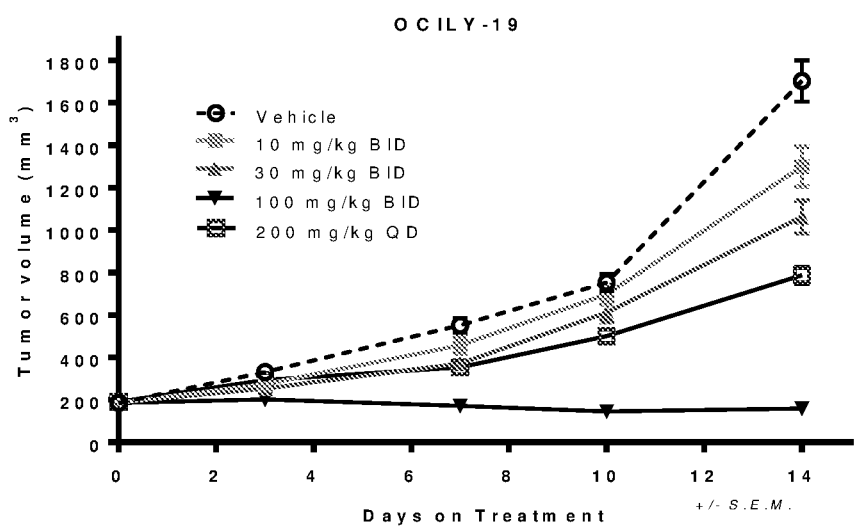
FIG. 9A shows OCILY-19 double hit diffuse large B cell lymphoma (DLBCL) tumor growth curves in CB17 SCID mice when left untreated (vehicle) or treated with 10 mg/kg of Compound 1, BID; 30 mg/kg of Compound 1, BID; 100 mg/kg of Compound 1, BID; and 200 mg/kg of Compound 1, QD, all measured over the course of 14 days.
Figure 9B:
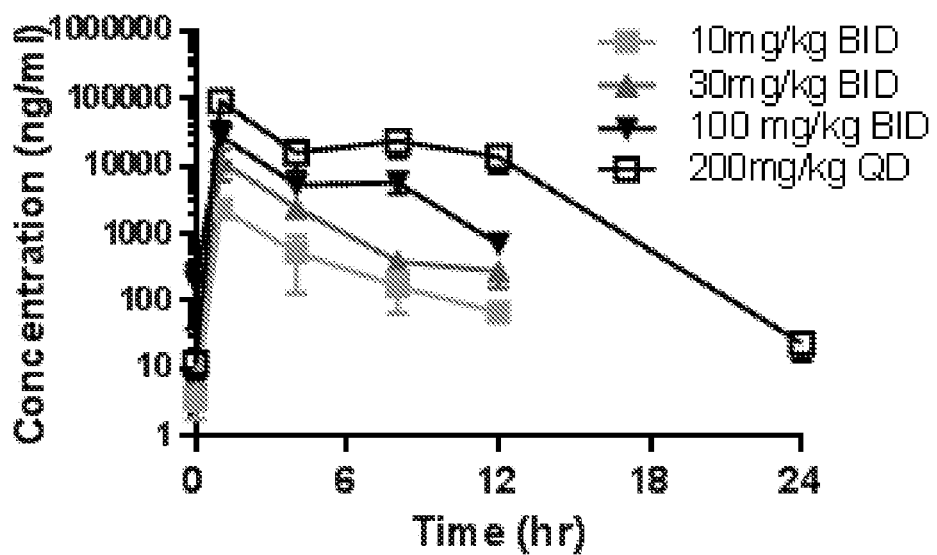
FIG. 9B shows the pharmacokinetic profiles of Compound 1, administered at the dosages described for FIG. 9A, in the plasma of the CB17 SCID mice, at the indicated timepoints following the last dose at end of study.
Figure 9C:
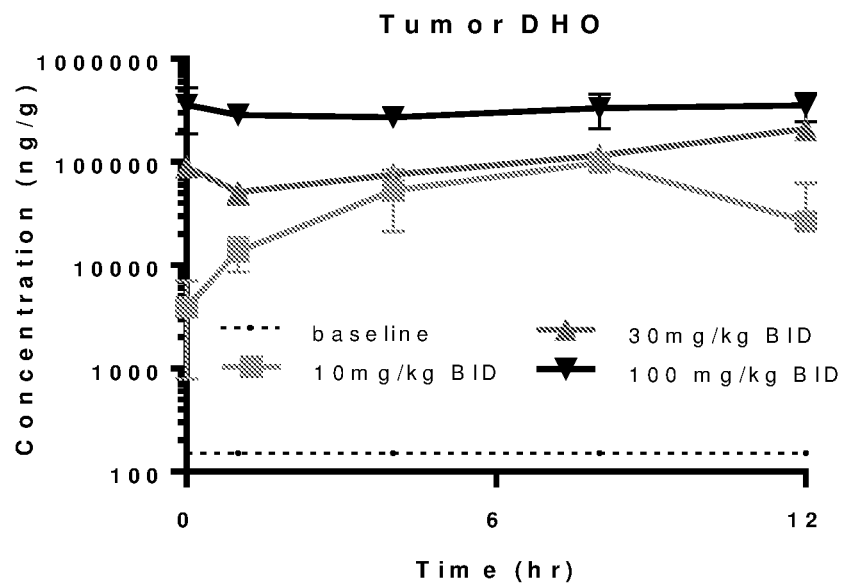
FIG. 9C shows the DHO levels in the untreated (vehicle) OCILY-19 tumors and tumors treated with compound 1 at the indicated doses, measured over the course of 12 hours following the last dose at end of study.
Figure 9D:
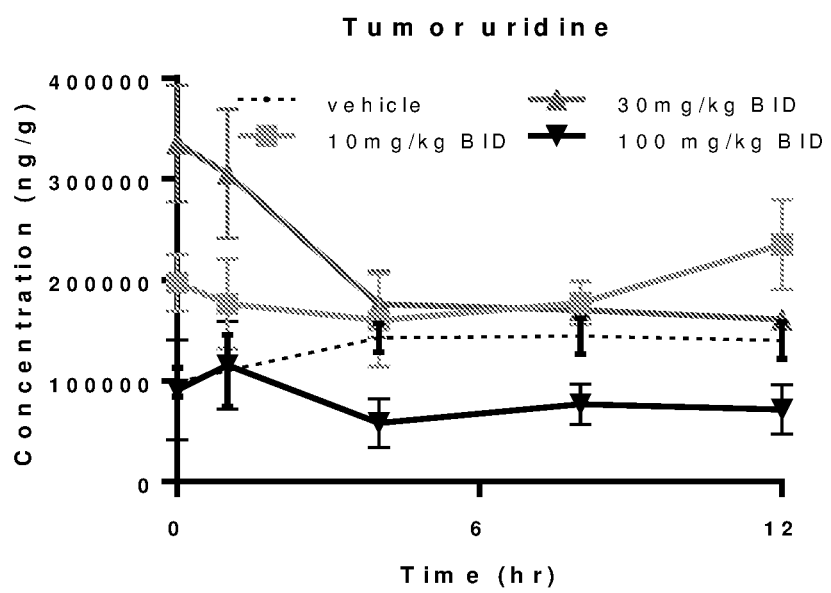
FIG. 9D shows the uridine levels in the untreated (vehicle) OCILY-19 tumors and tumors treated with compound 1 at the indicated doses, measured over the course of 12 hours following the last dose at end of study.

Degree of pathway modulation and tumor growth inhibition was demonstrated to be dose and schedule dependent (FIG. 9A). The 100 mg/kg BID dosing regimen resulted in superior efficacy compared to the 10 and 30 mg/kg BID dose arms and this correlated with a larger increase in tumor DHO (FIG. 9C) as well as a decrease in total tumor uridine pools (FIG. 9D). The 200 mg/kg QD regimen was less efficacious than the 100 mg/kg BID dosing regimen due to the short half-life of Compound 1 in mice, resulting in lower trough drug concentrations with QD dosing (see FIG. 9B).

In Vitro Growth Inhibition of Multiple Human Triple Negative Breast Cancer Cell Lines by Compound 1

Figure 10:
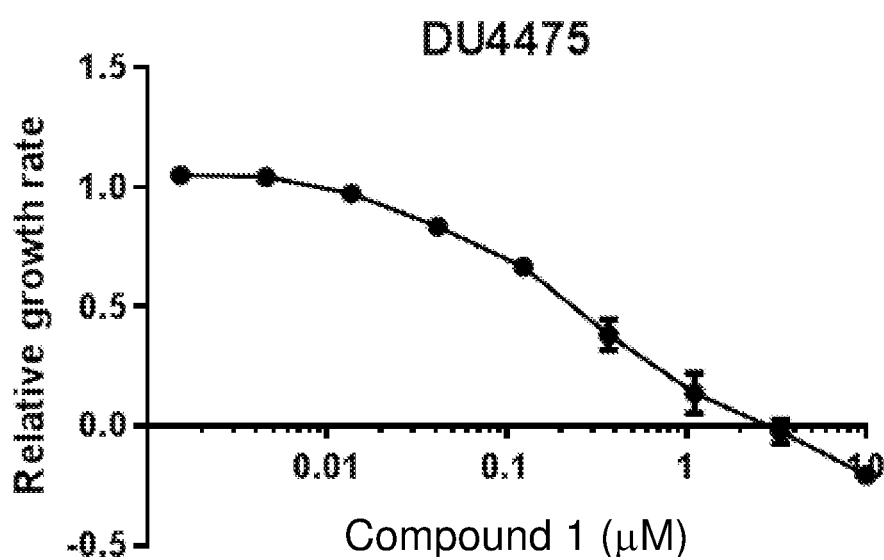
FIG. 10 is a curve showing the relative growth rate of the DU4475 triple negative breast cancer line treated with various concentrations of Compound 1 for 96 hours.

A panel of triple negative cancer cell lines (TNBC) were screened to evaluate whether a subset of TNBC could potentially benefit from treatment with compound 1 as a single agent. Treatment with Compound 1 for 96 hours robustly impaired cell viability/growth in DU4475 to a comparable degree as observed in cell lines of heme origin (see FIG. 10), while four other TNBC lines (HCC1143, HCC38, BTS49 and HCC1806) were insensitive under the conditions tested.

What is claimed is:

1. A method of treating a cancer selected from acute myeloid leukemia, multiple myeloma, B-prolymphocytic leukemia, non-Hodgkin's lymphoma, diffuse large B cell lymphoma, anaplastic large cell lymphoma, mantle cell lymphoma, triple negative breast cancer, melanoma, prostate cancer, and cancer of the esophagus, in a subject, comprising administering to the subject a therapeutically effective amount of Compound 1 represented by the following structural formula:

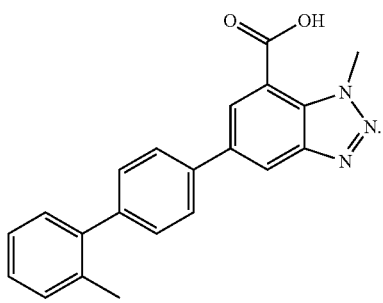 [SMILES: Cc1ccccc1-c1ccc(-c2cc(C(=O)O)c3c(c2)nnn3C)cc1]

2. The method according to claim 1, wherein the cancer is acute myeloid leukemia.

3. The method according to claim 1, wherein the cancer is multiple myeloma.

4. The method according to claim 1, wherein the cancer is B-prolymphocytic leukemia.

5. The method according to claim 1, wherein the cancer is non-Hodgkin's lymphoma.

6. The method according to claim 1, wherein the cancer is diffuse large B cell lymphoma.

7. The method according to claim 1, wherein the cancer is anaplastic large cell lymphoma.

8. The method according to claim 1, wherein the cancer is mantle cell lymphoma.

9. The method according to claim 1, wherein the cancer is triple negative breast cancer.

10. The method according to claim 1, wherein the cancer is melanoma.

11. The method according to claim 1, wherein the cancer is prostate cancer.

12. The method according to claim 1, wherein the cancer is cancer of the esophagus.

* * * * *